United States Patent [19]

Mantz

[11] 4,138,727
[45] Feb. 6, 1979

[54] SYSTEM FOR ANALYZING TIME-DEPENDENT PHENOMENA

[75] Inventor: Arlan W. Mantz, Acton, Mass.

[73] Assignee: Block Engineering, Inc., Cambridge, Mass.

[21] Appl. No.: 842,680

[22] Filed: Oct. 31, 1977

Related U.S. Application Data

[63] Continuation-in-part of Ser. No. 760,701, Jan. 19, 1977, Pat. No. 4,086,652.

[51] Int. Cl.² ............................ G01V 1/28; G01B 9/02
[52] U.S. Cl. ..................................... 364/525; 356/346; 364/819
[58] Field of Search ............... 364/525, 604, 819, 576, 364/580; 356/106 S

[56] References Cited

U.S. PATENT DOCUMENTS

| | | | |
|---|---|---|---|
| 3,989,938 | 11/1976 | Auth | 356/106 S |
| 4,086,652 | 4/1978 | Mantz | 364/525 |

*Primary Examiner*—Malcolm A. Morrison
*Assistant Examiner*—Errol A. Krass
*Attorney, Agent, or Firm*—Schiller & Pandiscio

[57] ABSTRACT

A system for analyzing a time-varying phenomenon in which the latter is repetitively initiated to provide a train of repetitive output signals. A fast Fourier transform interferometer is provied to scan the train. Data corresponding to a selected temporal resolution element having the same selected time position following initiation of each signal are sampled and the samples coded to improve signal-to-noise ratio. The time relation between a selected retardation point in the interferometer and the initiation of each signal in a given train is successively shifted so as to produce a series of coded data, each datum corresponding to a resolution element occurring at the selected time position but at a different interferometer retardation. The selected data are then assembled in their time sequence to generate a synthetic interferogram. The synthetic interferogram, when inversely transformed, provides the spectrum of the phenomenon as it occurred during the temporal resolution element at the selected time position.

8 Claims, 6 Drawing Figures

SYSTEM FOR ANALYZING TIME-DEPENDENT PHENOMENA

This application is a continuation-in-part of the co-pending application Ser. No. 760,701 now U.S. Pat. No. 4,086,652 for Method and Apparatus for Analyzing a Time-Dependent Phenomenon filed Jan. 19, 1977.

This invention relates to systems for time-resolving data, and particularly to the time resolution of data multiplex-encoded into a single channel.

For example, conventional analysis of spectral phenomena typically involves a plurality of observations of each spectral element over a period of time. Such observation can be made in parallel along a like plurality of channels or can be made sequentially over a single channel. Effectuation of such a series of sequential observations is highly inefficient because the total time during which any one resolution element (e.g. a particular wavelength band) can be observed practically is quite limited. Additionally, the observation of each resolution element implies that all of the other data are discarded or unused during the particular observation time. A resolution element here can be defined as the number of samples to be taken of a phenomenon, divided by the total time required to obtain the totality of samples.

Fourier transform spectroscopy provides a substantial improvement over the classical dispersive techniques exemplified by a conventional spectrometric single channel method. A Fourier transform spectrometer provides a sequence of data generated on a single channel and arising from the modulation of all wavelengths of input light with a separate carrier frequency. The separate wavelengths can then be discriminated from one another by frequency filtering, the amplitude of each frequency being proportioned to the intensity of the light at the wavelength corresponding to that frequency. Such an interferometer spectrometer can thus measure wavelength for a time $N/2$ (where $N$ is the number of resolution elements) longer than the time required to obtain similarly resolved measurements with conventional spectroscopes. The improvement in accuracy gained by using an interferometer spectrometer (i.e. the square root of $N/2$) is known as Felgett's advantage or the multiplex advantage, and is described in detail by L. Mertz, *Transformations in Optics*, Chap. I, John Wiley & Sons, Inc., (1965). Such Fourier transform spectroscopes usually either employ stepping interferometers with gated detector signals or incorporate rapid scan techniques. The former imposes severe limits on instrument stability as well as source life time; the latter imposes severe limits on maximum achievable resolution, signal-to-noise ratio and time resolution.

Spectroscopy with a rapid scan interferometer has been considered most useful with steady-state or quasi steady-state light sources because, as Mertz points out, where there is source modulation, the noise level increases by $N/2$, as compared with Felgett's advantage of square root of $N/2$, leaving a net inferiority of a factor of the square root of $N/2$. In effect, the modulation of the source is considered to act as a factor similar to a truncating function. For the foregoing reasons, the use of Fourier transform spectroscopy to examine time-varying spectral phenomena has been largely neglected despite the extremely efficient throughput of a Fourier transform spectroscope.

R. E. Murphy et al in "Time-Resolved Fourier spectroscopy" Journal of the Optical Soc. of America, Vol. 65, No. 5, May, 1975, pp. 600–605 suggests that Fourier spectroscopy can be used to investigate time-dependent spectral sources. Murphy et al observed with an interferometer-spectrometer a series of phenomena each at a different fixed path retardation, synthesized from the data a set of time sequenced interferograms and transformed the time-sequenced interferograms to obtain the recovered spectra at successive time intervals. However, the Murphy et al technique, using stepped retardation, is subject to the limitations on instrument stability and source life time above noted and is highly sensitive to amplitude variation among the several phenomena observed.

The present invention overcomes problems of the prior art by employing both temporal and spectral multiplexing with a transform system which allows high resolution and signal-to-noise even with data with microseconds resolution time. A principal object of the present invention is therefore to provide means for a method of analyzing transient phenomena using both temporal and spectral multiplexing. While the system can be used with any of a large number of data gathering devices (such as pulsed NMR and NQR systems, Hademard spectrometers and the like) particularly, the present invention has an important object the use of a continuous scanning Michelson interferometer for spectral study of kinetic systems using both temporal and spectral multiplex techniques.

To effect the foregoing and other objects, the present invention generally is embodied in a system for time resolving a sequence of data derived from a phenomenon, which system comprises repetitive initiation of the phenomenon, detection of each occurrence or cycle of the phenomenon and the repetitive convolution with a transformation (as by continuous, controlled-velocity, repetitive, interferometric scanning) to provide an ordered set of interferograms each being representative of the course of each cycle of the phenomenon. By establishing the repetitive scanning cycle and the repetition of phenomenon initiation at different repetition rates, the scanning, and excitation cycles therefore are shifted in time in ordered increments with respect to one another preferably until the intitial temporal relation between initiation and sampling is restored. The term "interferogram" as herein used refers particularly to a self-reciprocal transform of a time sequence of input data, e.g. a Fresnel, Fourier, Dirac or other such transformation where the input data are spectral, sonic or the like. From the first set of interferograms, at least one "time average" interferogram is synthesized from a plurality of data moieties or points, each being at the same selected fixed position (in time) on each of the first set of interferograms with regard to initiation of the phenomenom. The "time averaged" interferogram (or second set of interferograms as the case may be) is then analyzed or subjected to the inverse of the initial transform to produce a data set representing the phenomenon as it occurred at that fixed data point in time following initiation of the phenomenon, i.e. the data set is constant in "source" time. Alternatively, each interferometer scan is sampled only once at a present time following initiation of the phenomenon, all samples taken during scans having the same retardation phase relative to initiation being coadded to provide an average signal. The time relation between a selected retardation point in the interferometer and phenomenon initiation is periodically shifted to produce a series of such average signals. The latter can be assembled in time sequence to synthesize the "time averaged" interferogram.

Other objects of the invention will in part be obvious and will in part appear hereinafter. The invention accordingly comprises the apparatus and method possessing the construction, combination of elements, and arrangement of parts which are exemplified in the following detailed disclosure, and the scope of the application of which will be indicated in the claims. For a fuller understanding of the nature and objects of the present invention, reference should be had to the following deetailed description taken in connection with the accompanying drawings wherein:

The present invention can advantageously be described typically in connection with scanning interferometric means as an examplary means for generating interferograms each being representative of at least some stage in the progression of a phenomenon being observed. The latter, for examplary purposes here, will be considered to be the photolytic decomposition of acetone vapor by ultraviolet radiation, although it should be appreciated that a very large number of phenomena are susceptible of analysis by the present system. For example, the invention can be employed in basic chemical kinetics studies, isotopic separation processes, laser fusion phenomena, photochemical ionization and free radical phenomena, relaxation phenomena and the like. The present invention is particularly useful in study and analysis of processes in which excitation occurs within $10^{-6}$ to $10^{-8}$ seconds, and after approximately $10^{-4}$ seconds the excited medium relaxes eithin about a $10^{-3}$ to $10^{-1}$ second period.

Figure 1:
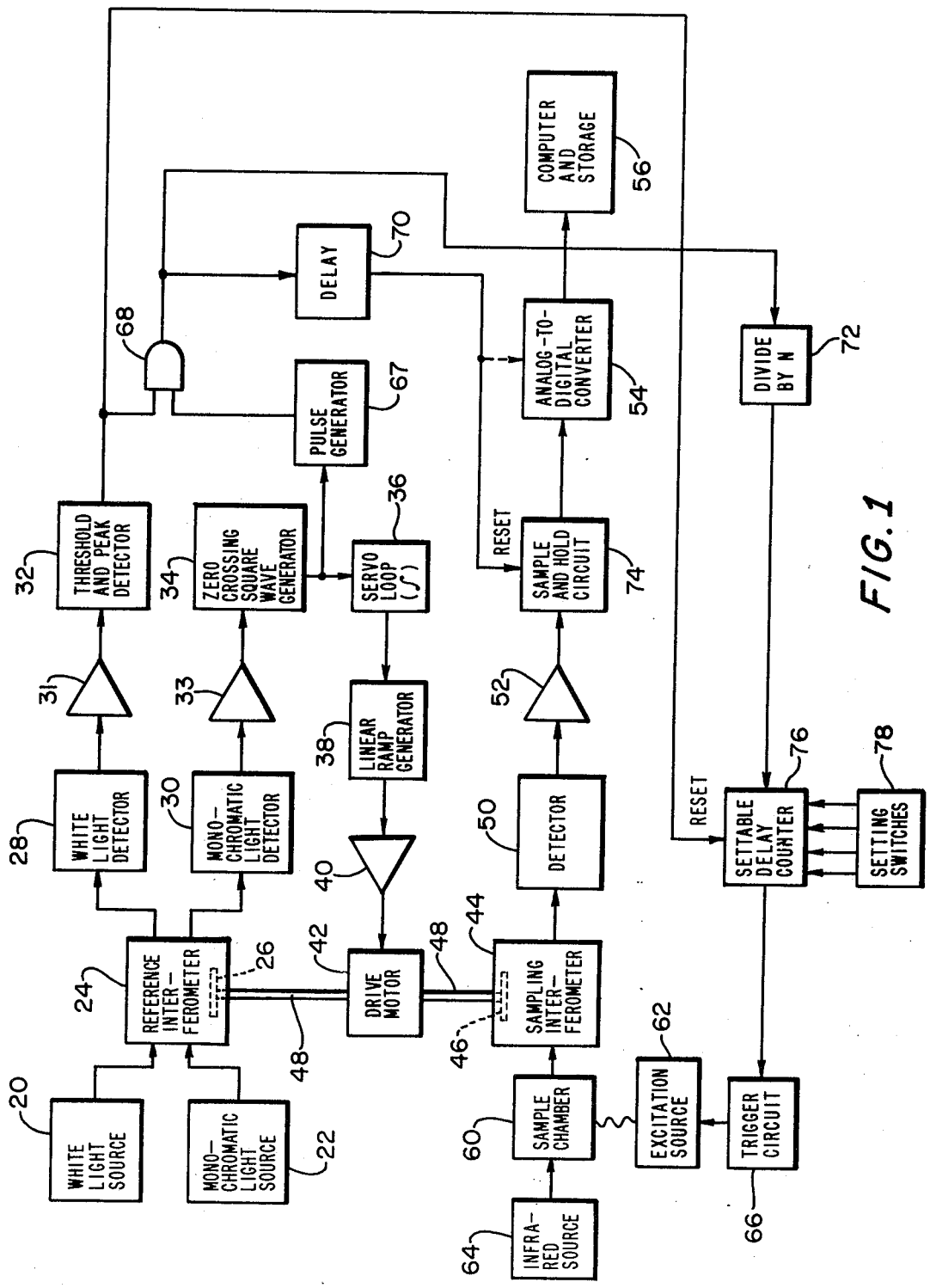
FIG. 1 is a schematic block diagram of a system embodying the principles of the present invention.

As typical scanning interferometric means, one can use a Digilab Model FTS-20, commercially available from Block Engineering, Inc., Cambridge, Massachusetts. As shown in FIG. 1 such an interferometric means typically includes white light source 20 and monochromatic light source 22, both positioned to illuminate the entrace aperture of reference interferometer 24. The latter typically is a Mechelson interferometer in which the scanning element serving to modulate input radiation to provide an interferogram thereof, is a movable mirror shown schematically at 26.

Positioned in known manner to detect the modulated interference pattern produced by reference interferometer 24 are broad band white light detector 28 and monochromatic light detector 30, it being understood that these detectors include any filters necessary to discriminate between the interference patterns respectively produced in response to the respective light sources. White light detector 28 typically produces an electrical signal as a function of the white light interference pattern or interferogram generated by reference interferometer 24. The electrical output of detector 28 is coupled to the input of amplifier 31 and the output of the latter is connected to the input of a threshold-and-peak detector circuit 32.

Similarly, detector 30 provides an electrical signal as a function of the light input thereto, to the electrical output of detector 30 is coupled to the input of amplifier 33. The output of amplifier 33 is connected as an input of zero-crossing square wave generator 34. The latter typically is simply an axis-crossing detector circuit, the output of which is coupled to the input of a monostable multivibrator or one-shot to trigger the later to produce a square wave when an axis-crossing is detected. Both circuits being well known in the art so need no further delineation. The output of axis-crossing detector 34 is connected to the input of integrating servo loop circuit 36. The output of servo loop circuit 36 is connected to the input of linear ramp signal generator 38. The output of the latter is connected through power amplifier 40 as the input to drive motor 42, typically a solenoid-type reciprocating motor.

The interferometric means also includes sampling interferometer 44, substantially the same as reference interferometer 24, in which the scanning element which serves to modulate input radiation is shown schematically and typically as mirror 46. Both mirror 46 and mirror 26 are connected by a mechanical coupling (shown schematically at 48) to motor 42 so as to be driven synchronously by the latter.

Disposed with respect to interferometer 44 so as to detect the interference pattern of interferogram produced by the latter, is detector 50 which serves to convert the optical interferogram into a corresponding electrical signal. The electrical output of detector 50 is coupled through amplifier 52 to the input of analog-to-digital converter 54, and the output of the latter is connected through appropriate interfacing (not shown) to computer 56. The interferometric means thus described is essentially the prior art basic structure of the aforesaid commercial FTS-20 device. Computer 56 is typically a Nova Model 2/10 computer (commercially available from Data General Corporation, Southboro, Massachusetts coupled to a 1.2 million word moving head disc for temporary data storage and a digital magnetic tape for permanent data storage and constitutes a convenient form of means for selecting from each interferogram of an ordered set, a data point corresponding to a time resolution element of interval occurring at a fixed time position following initiation of the phenomenon, and for combining the data points in the same order as the ordered set to synthesize a second interferogram representing the convolved data only at that time position. It will be apparent to those skilled in the art that a dedicated special purpose digital computer or hard-wired analog system could readily be substituted in place of computer 56.

The means for repetitively initiating the phemonemon to be analyzed includes sample chamber 60 in which the phemonemon is to be initiated, and triggerable excitation source means 62 for exciting the phemonenon of interest in chamber 60 at selected times. Typically, chamber 60 is an enclosure such as a 30 centimeter long quartz absorption cell equipped with KBr windows to permit detection of the phenomenon by infrared absorption. To this end, infrared souce 64 is disposed for illuminating sample chamber 60 such that interferometer 44 can modulate infrared radiation emitted from chamber 60 following any infrared absorption occurring in the course of the phenomenon. Excitation source means 62 can be any of a number of systems, but typically, for the example of photolytic decomposition chosen here, is a triggerable ultraviolet flash lamp system as a 1540 Strobolume system (commercially available from General Radio Company, Concord, Massachusetts) which can provide a ¼ joule output intensity 10 $\mu$ sec. full width, half-maximum light pulse.

Source 62 is also connected to be controlled by trigger circuit 66. Thus the source can be triggered at any selected time at any of a number of selected rates. The output of generator 34 is connected to the input of pulse generator 67, typically a Schmitt trigger circuit, the output of the latter being connected together with the output of detector circuit 32 as inputs to AND gate 68. The output of the latter is connected to the inputs of both delay circuit 70 and divider 72. Delay circuit 70 which simply serves to introduce, in known manner, a time delay into signal propagation, has its output connected to the reset input terminal of sample-and-hold circuit 74.

The system of the present invention provides means for converting into digital form each sequence of data produced by interferometer 44. To this end, the data input terminal of circuit 74 is connected to the input of analog-to-digital converter 54, so that circuit 74 serves as a sampling linkage between interferometer 44 and computer 56.

Divider 72, a typical digital "divide-by-N" circuit, has its output connected to the count input of a settable delay means such as counter 76. The count in the latter is typically controlled or selected by manually operable setting switches 78 such as thumb wheel switches or the like. Lastly, the output of detector circuit 32 is also connected as an input to the reset terminal of counter 76.

Figure 2:
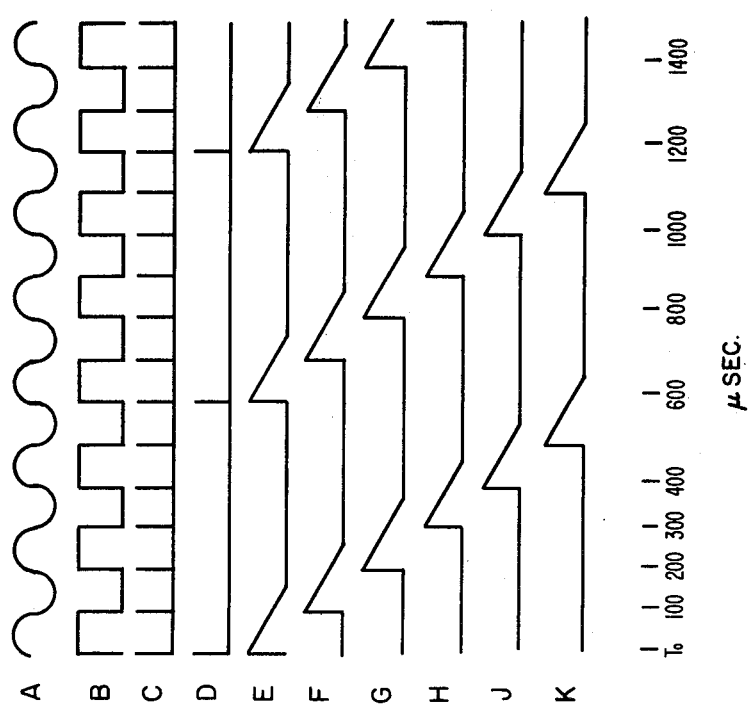
FIG. 2 is a number of representative idealized waveforms on a common time base, of signals appearing at various points in a system of the type shown in FIG. 1.

In operation, drive motor 42 is driven by a linear ramp or sawtooth signal from generator 38 so that mirrors 26 and 46 have a displacement velocity of approximately 0.3cm/sec. The light from source 22 (typically an HeNe laser which provides an output at 6328 Å) is modulated by the motion of mirror 26, and because the mirror motion is linear, detector 30 and amplifier 33 provide a sinusoidal output (shown schematically at FIG. 2A) with a period of approximately 100 microseconds. Similarly, white light detector 28 will provide a well known white light interferogram as the path retardation of interferometer 24 changes with the motion of mirror 26. Such a white light interferogram characteristically possesses a maximum or peak intensity at the point of zero path retardation. The output of amplifier 33 is converted in generator 34 to a square wave such a shown in FIG. 2B. The square wave output of generator 34 is applied to the input of circuit 36 wherein the square wave is integrated. Thus, the output of circuit 36 will provide a zero signal when the duty cycle of the input square wave is exactly fifty percent, but any variation in the duty cycle will result in a corresponding error signal being provided at the output of error signal 36. This error signal when applied to linear ramp generator 38, changes the slope of the ramp provided by generator 38 in such a direction as to alter the velocity of mirrors 26 and 44 so as to restore the duty cycle of the output of generator 34 to precisely fifty percent.

The system, therefore, constitutes a closed loop which insures that the frequency of the output of generator 34 is closely maintained at the desired value.

Detector circuit 32 provides an output signal which serves to enable gate 68 only at some time, $t_0$, the zero path retardation peak seen by detector 28. Hence, all timing in the system can be controlled to operate from the point of zero retardation in each scanning cycle provided by interferometer 24. It will be appreciated that at the end of each excursion of mirror 26, a scanning cycle of the interferometer has been completed and that the interferometer must be reset. The controls which reset ramp generator 38 and reverse drive motor 42 and reset the output of detector 32 are not shown for the sake of clarity in exposition, but are well known and are part of the typical interferometer-spectrometer currently commercially available.

When gate 68 is enabled at $t_0$, it passes a train of clock pulses produced by pulse generator, each pulse representing an axis crossing of the square wave produced by generator 34. A typical train of pulses is shown in timed relation in FIG. 2C. The pulse train is applied to divide-by-n circuit 72 which, therefore, provides an output pulse train, such as is shown in FIG. 2D wherein n = 6 for exemplary purposes, haing a repetition rate which is 1/n of the repetition rate of the output of gate 68. The pulse train of FIG. 2D is applied, after having been passed through delay 76, to actuate trigger circuit 66 and excite source 62 into emission. The output of excitation source 62 is shown schematically in FIG. 2E wherein the signal or flash, corresponding to the triggering pulse of FIG. 2D, rises to a maximum and and then decays to a minimum, for example, with full width at half-height of 100 microseconds. The period between pulse or initiation of the output of excitation source is, of course, 600 microseconds, corresponding to the pulse repetition rate of the output of circuit 72. This sequence of events continues with the excitation source being triggered at 600 microsecond intervals until the end of an interferometer scan in interferometer 44, whereupon the pulse train from gate 68 is terminated until the next scan has commenced and an appropriate synchronizing axis-crossing just after a zero retardation peak detection by detector 32 has occurred. Each excitation flash occurring during an interferometer scan initiates the phenomenon of interest, e.g. the photolytic decomposition of acetone in chamber 60. During the course of the decomposition, the spectral changes due to absorption of infra-red from source 64 are observed by interferometer 44 which convolves the observed spectrum with a fast Fourier transformation to produce, as well known, an interferogram. In order to provide an acceptable signal-to-noise ratio, a number of identically scanned interferograms can be coadded either through analog methods as described in U.S. Pat. No. 3,286,582 to L. Mertz, or by conversion to digital form and addition in the computer. In the example here described, the interferogram collected in one complete scan with a duration from zero retardation of 0.12 seconds, would include data derived from about 200 excitation source flashes. The number of excitation source flashes per interferometer scan, (or the number of scans per flash as the case may be) depends upon the relative length of time during which the phenomenon of interest continues (or decays) and the time period of the scan cycle, so the ratio of flashes to scans is largely a matter of choice.

Delay counter 36 is then set by setting switches 78 to interpose a one pulse period (100 microsecond) delay so that the time history of the subsequent excitation source pulses becomes as shown in FIG. 2F, i.e. is shifted by a time increment with regard to the zero retardation peak position of the interferometers. When sufficient interferograms have been obtained using the sequence of 5 flashes of FIG. 2F, and appropriately coadded to improve signal-to-noise, the delay in counter 76 is again reset by adding another 100 microsecond delay period resulting in a time history of excitation source outputs somewhat as shown in FIG. 2G. Similarly, by altering the delay provided by counter 76 by successive 100 microsecond increments, one obtains an ordered set of excitation pulse histories such as is shown in FIGS. 2H, J and K. It will be appreciated then that for each of the excitation source histories shown in FIGS. 2E through 2K inclusive, one obtains a similarly ordered set of corresponding interferograms. These interferograms contain all of the source spectral information and the source temporal history with a two microsecond resolution, each resolution element being displaced by 100 $\mu$secs from the next resolution element of 2 $\mu$sec. Interferograms as produced at the output of detector 50 and amplified by amplifier 52 are, in well-known manner, sampled by sample-and-hold circuit (preferably using a 2 microsecond or less interval) and each sample is converted by analog-to-digital converter 54 to digital form for storage as an ordered set in computer 56.

Preferably, delay 70 is adjustable by 0.5 $\mu$sec increments to fine tune by interposing a delay in actuating sample-and-hold circuit by the 100 $\mu$sec period pulse train from gate 68. This serves to permit sampling of data to be delayed, relative to triggering of excitation source 62, to match or compensate for the usual rise time of the phenomenon in response to excitation.

From the data thus provided and stored in computer 56, one however can look at the spectrum of material in sample chamber 60 within a two microsecond resolution range or time domain. For example, if one wishes to look at the nature of the spectrum in the zero-100 microsecond time domain, one takes the data moieties or information taken during the first, seventh, thirteenth, etc., resolution elements (each of two microsecond duration) from the first interferogram corresponding to the excitation due to the excitation source history shown in FIG. 2E; the data moieties from the second, eighth, fourteenth, etc., resolution elements of the interferogram next in order and corresponding to the source history shown in FIG. 2F; the information taken during third, ninth, fifteenth, etc. resolution elements of the interferograms third in order and corresponding to the excitation source history of FIG. 2G, etc. until all stored interferograms have been sampled, and construct a new or synthetic interferogram in which each of the data moieties are placed in sequence according to the order of the original interferograms in the set. The software sorting routine needed to construct a synthetic interferogram corresponding to one time-resolution element can be constructed in the following manner, using a notation in which a letter in parentheses identifies the original interferogram by the letter caption of the excitation source history of FIG. 2, and the number in the parentheses is the ordinal value of $t_o$ from the selected time resolution element in units of 100 microseconds. For example, the notation for the temporal resolution element at 400 $\mu$secs after $t_0$ in the interferogram, corresponding to the temporal source history shown in FIG. 2G would be (G,4). Thus, synthetic interferogram for the first 100 microsecond interval of the original interferograms would be constructed by placing in sequence the data corresponding to the following (E1) (F2) (G,3), (H,4), (J,5), (K,6), (E,7), (F,8), (G,9), (H,10), (J,11), (K,12), etc. A formal software program for effecting the foregoing in a Data General 2/10 computer is attached to copending application Ser. No. 760,701 earlier identified.

Once an interferogram has been synthesized and stored again in the computer, the latter is preferably programmed to perform the inverse transformation on the synthetic interferogram to obtain the information, such as the spectrum, as it was observed during the time interval or resolution element to which the synthetic interferogram corresponds. The programs required to perform a fast Fourier transformation by digital computer, such as the Cooley-Tukey algorithm are well known in the art. Alternatively, in place of a digital computer, one can use an analog system such as heterodyne wave analyzer to perform the desired inverse transformation.

Figure 3:
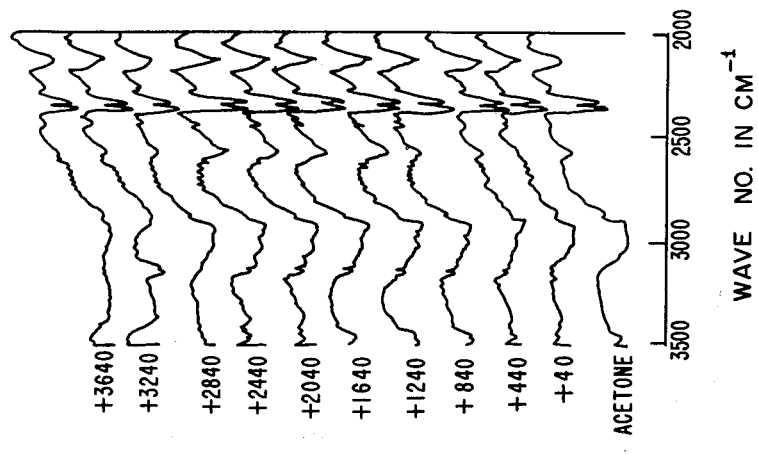
FIG. 3 shows representative spectra obtained by transformation of interferograms synthesized from other interferograms taken during photolytic decomposition of acetone.

The above detailed invention was used to investigate ultraviolet photolysis of a number of materials, particularly acetone and acetaldehyde. Using the flash lamp hereinbefore described as source 62, one obtained quarter joule peak intensity, 10 $\mu$sec full width half-maximum light flashes. The flash lamp operated at 250 flashes per second. A series of interferograms were taken and synthetic interferograms were formed and inversely transformed. The various time-dependent spectra are shown in FIG. 3, each representing a 2 $\mu$sec interval, 400 $\mu$secs apart, each identified by the time in microseconds from $t_o$. The bottom spectrum in FIG. 3 however is a single beam spectrum of acetone (so labeled) with no UV exposure.

The time dependence of spectral features in FIG. 3 is obvious. The sampling interferometer was not purged, therefore the atmospheric $CO_2$ feature is present in each spectrum at 2349cm$^{-1}$. Photodecomposition of acetone produces CO with a band origin at 2149cm$^{-1}$ superimposed upon the acetone band.

The spectral feature with a band origin at 3138cm$^{-1}$ demonstrates the utility of the invention. This sequence of experiments was undertaken to study the reaction as it occurred in the well known dissociation scheme

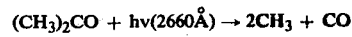

Several unexpected features were observed. The spectral feature at 3138cm$^{-1}$ which has been tentatively identified as due to ketene absorption, forms after the UV flash, increases in concentration until 3.24 milliseconds, and disappears in the next 0.40 millisecond.

Other spectral features between 2500 and 2800 cm$^{-1}$ appear in emission 40 microseconds after the UV flash. By 1.24 milliseconds this system is absorbing and at 3.64 milliseconds the system is once again emitting.

Figure 4:
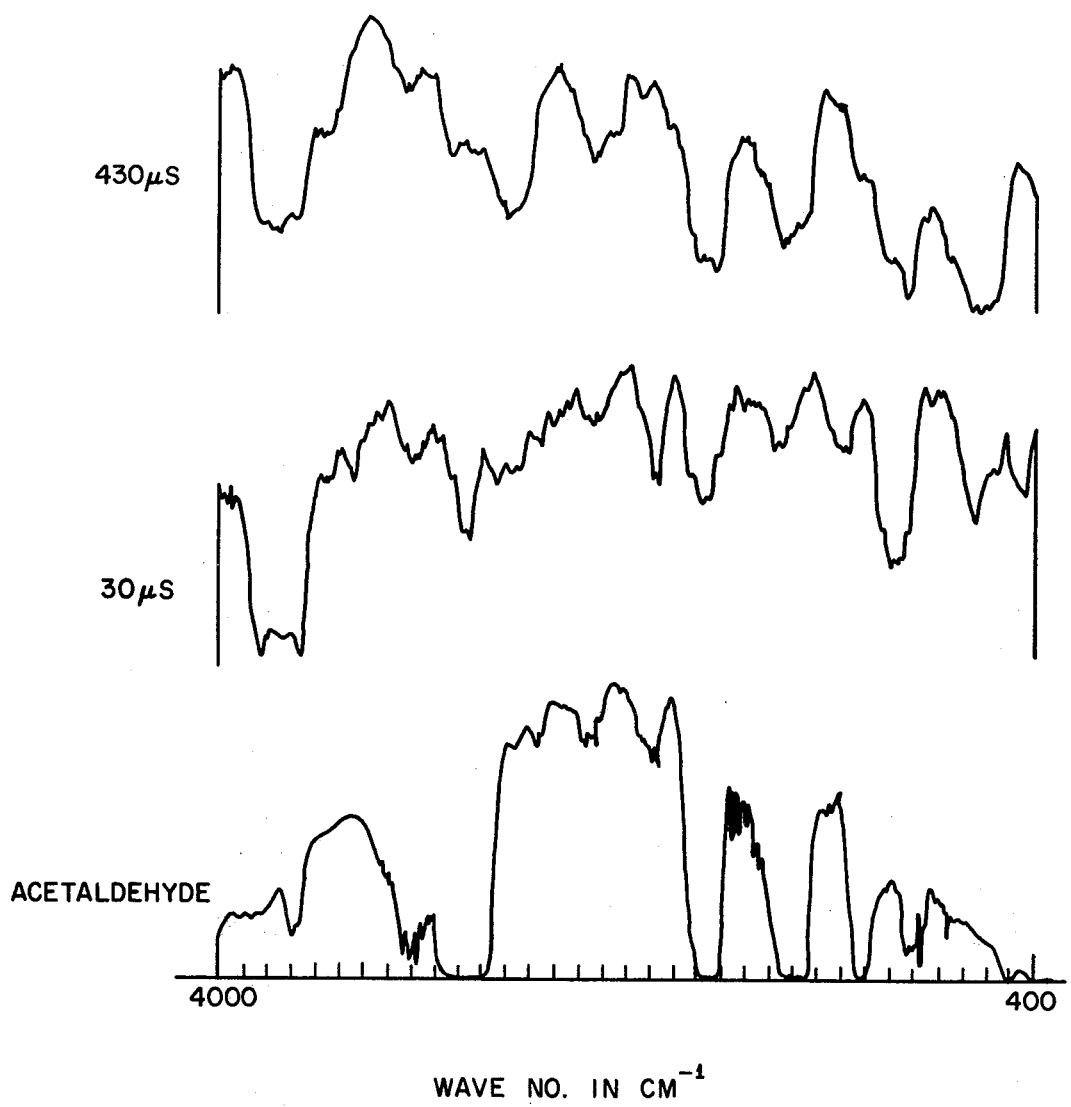
FIG. 4 shows representative spectra obtained by transformation of some synthetic interferograms derived from the photolysis of acetaldehyde.

A similar series of spectra shown in FIG. 4 (compared to the spectrum taken without UV exposure at the bottom of FIG. 4) were derived from acetaldehyde UV photolysis according to the present invention. The very substantial changes occurring between 30 $\mu$sec and 430 $\mu$sec following UV exposure can readily be observed.

Figure 5:
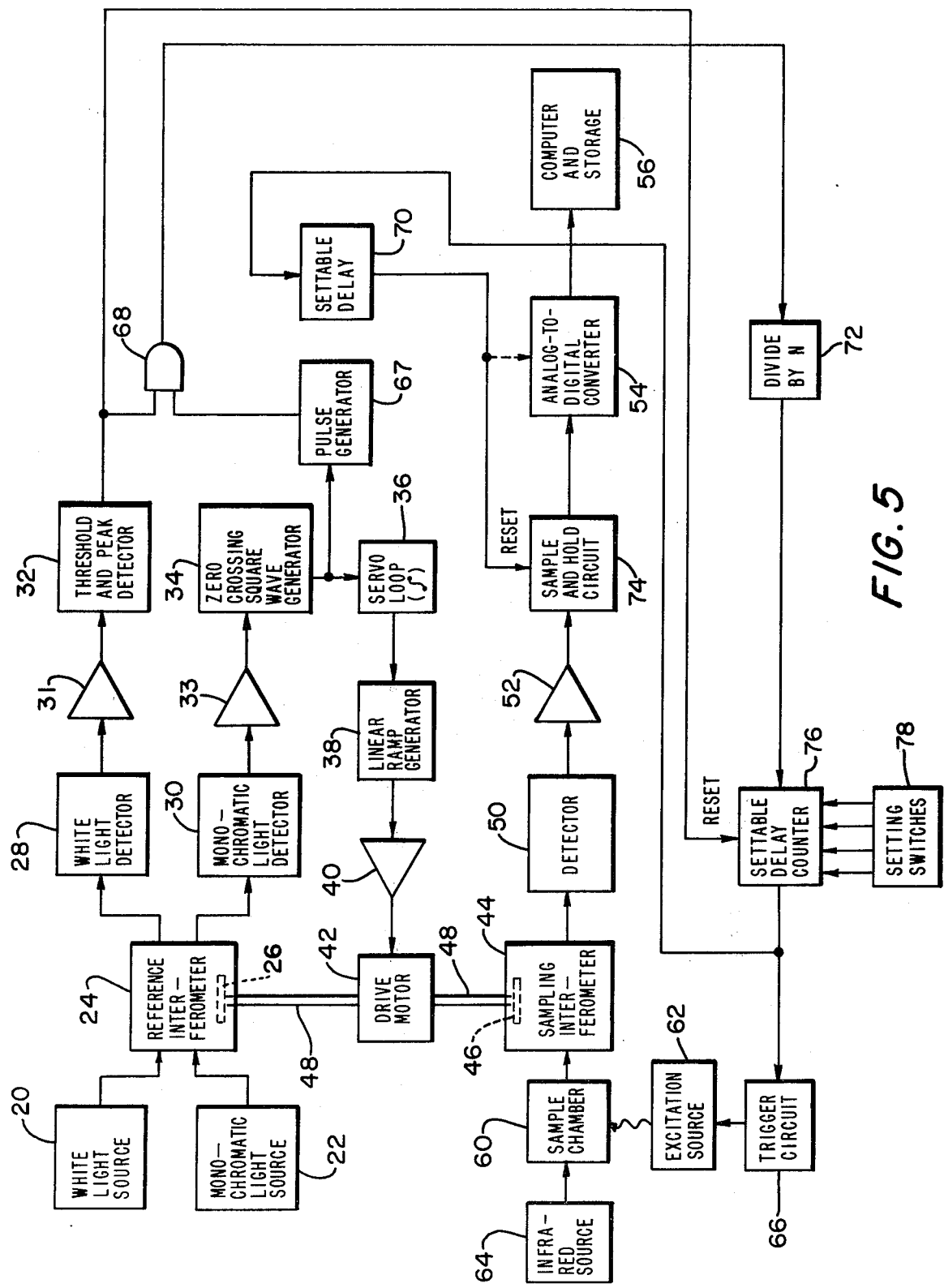
FIG. 5 is a schematic block diagram of an alternative version to the system of FIG. 1.

In the alternative form of the device of FIG. 1, as shown in FIG. 5, like parts are indicated with like numerals. Thus, the device of FIG. 5 includes the same interferometric means comprising the same parts as shown in FIG. 1, the output of both pulse generator 67 and of detector circuit 32 comprising the input to AND gate 68. The output of the latter however, is only connected to the input of divider 72.

The circuit of FIG. 5 also includes a typical settable delay means such as counter 76, the count in which is controlled or selected by manually operable setting switch 78. The output of delay means 76 is connected to the input of trigger circuit 66. The output of counter 76 however is also coupled as the input to delay circuit 70. The output of delay circuit 70 is connected, as in the embodiment of FIG. 1, to the reset terminal sample-and-hold circuit 74.

Figure 6:
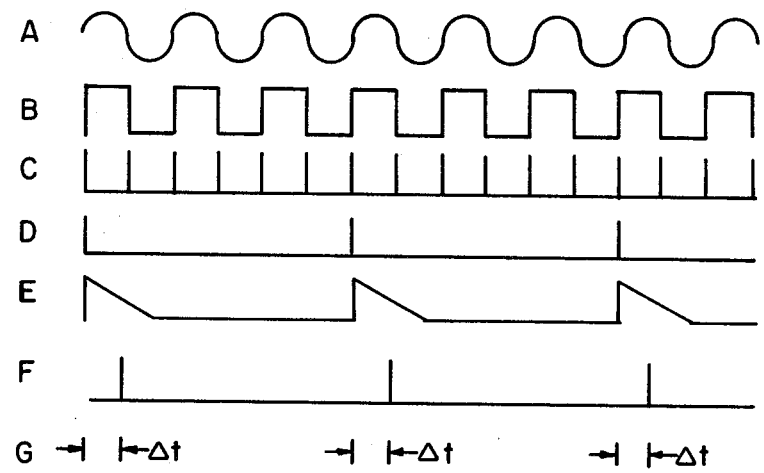
FIG. 6 is a number of idealized waveforms on a common time base of signals appearing at various points in a system such as that shown in FIG. 5.

The operation of the device of FIG. 5 provides in a similar manner an output from gate 68 similar to that of the device of FIG. 1, so that as gate 68 is enabled at $t_0$, the train of clock pulses from generator 67, as shown in FIG. 6A, is applied to divider circuit 72. The latter, as in the device of FIG. 1, provides the same pulse train (shown in FIG. 6B) which is applied, after being passed through settable delay circuit 76, to activate trigger circuit 66 and thus excite source 62 into emission as shown in FIG. 6C. The same pulse train from delay circuit 76 is also however applied through delay circuit 70 to the reset terminal of sample-and-hold circuit 74 (or alternatively to actuate A-D converter 54).

As in the system of FIG. 1, the number of excitation flashes (a consequent emissions from chamber 60) per interferometer scan depends on the number of excitation pulses applied to source 62 by circuit 76 during each scan. Circuit 76 selectively establishes the relative phase between the scan cycle and the excitation pulse train in FIG. 6B in accordance with the setting of switches 78. However, the application of the same pulse train, each pulse being delayed by a predetermined interval $\Delta t$ in delay circuit 70 to either circuit 74 or A-D convertor 54 causes sampling of each of the emissions from chamber 60 to occur only once (typically over a 2$\mu$sec sampling window) in the decay curve at some point in time, $\Delta t$, after initiation of the emission, quite unlike the system of FIG. 1 where sampling occurs much more frequently during the decay of each emmission. In order to permit one to select $\Delta t$, delay 70 in FIG. 5 is preferably a settable delay such as delay 76 in FIG. 1. Hence one can obtain sampling at a selected point in time in each life time of the multiplicity of emmissions observed, for a given retardation, and by coadding the samplings in known manner as hereinbefore noted, above the signal-to-noise ratio of that time sample taken at the specified retardation and time interval $\Delta t$.

As each set of emission curves is successively time-shifted by a time increment established by delay circuit 76 with regard to the zero retardation peak position of the interferometers, the sampling point remains the same with respect to initiation of the excitation curve, but shifts by that same time increment with regard to the zero retardation peak. Hence, the successive sets of samples, (each set representing a summation of samples taken at a selected retardation but at the same point in time following initiation of the emission phenomenon of interest) can simply be ordered in time to synthesize a single interferogram, which when inversely transformed as hereinbefore noted, yields the desired spectrum at that point in time in the occurrance of the emission phenomenon of interest.

A formal software program for effecting the foregoing operation of the embodiment of FIG. 5 in a Data General 2/10 computer is attached hereto as Appendix A.

The system of FIG. 5 thus simply yields one interferogram representing the spectrum of the phenomenon of interest at a time $\Delta t$ after initiation of the phenomenon of interest, whereas the system of FIG. 1 produces a plurality of different timed spectra. Where only a single time spectrum is desired so that the other spectra obtained for the device of FIG. 1 are superfluous, the system of FIG. 5 will then be useful to avoid obtaining undesired or redundant data and therefore offers substantial time economy and particularly reduces data storage requirement.

Since certain changes may be made in the above apparatus and process without departing from the scope of the invention herein involved, it is intended that all matter contained in the above description or shown in the accompanying drawing shall be interpreted as illustrative and not in a limiting sense.

APPENDIX A

```
0001  MAIN MACRO REV 04.00              15:04:47 01/13/77
01                ;PROGRAM ITC - INITIALIZE TRS CONTROLLER
02                ;
03                ;9/28/76 - RCS
04                ;
05                ;RESIDES IN SECTOR 206
06                ;
07
08      020000 DATA=20000        ;(BIT 2) BIT PATTERN IN CONTROL REGISTER
09      010000 STROBE=10000      ;(BIT 3)
10      020000 SENSE=20000       ;(BIT 2) BIT PATTERN IN INPUT REGISTER
11
12      002200 BUF=2200          ;ADR OF INPUT BUFFER
13
14      000150 EXEC=JMP 150      ;RETURN TO THE EXEC
15      002017 ABORT=JMP #17     ;ABORT THE COMMAND LIST
16
17      006276 DREAD=JSR #276    ;DISK READ, (AC1=CORE, AC0=DISK)
18      006277 DWRIT=JSR #277    ;DISK WRITE (DITTO)
19      006273 DWAIT=JSR #273    ;DISK WAIT ROUTINE
20
21      000172 PFINFO=172        ;ADR IN CORE FOR FINFO DISK SECTOR
22
23      000200 ATD=200
24      000201 FED=201
25      000202 FPD=202
26      000203 NOE=203
27      000204 FFI=204
28      000205 CAD=205
29      000206 MOD=206
30
31      000207 XATD=207          ;AREA FOR SAVING INFRO FROM CONTROLLER
32      000210 XFED=210
33      000211 XFPD=211
34      000212 XNOE=212
35      000213 XCAD=213
36      000214 XMOD0=214
37      000215 XMOD1=215
38      000216 WNOE=216          ;WORKING NOE VALUE
39
40      000220 TYPLOC=220
41
42            .MACRO MOVE
43                  JSR .MOVE         ;MOVE A BLOCK OF CORE
44                  A1                ;FROM
45                  A2                ;TO
46                  A3                ;- # OF WORDS TO MOVE
47            %
48
49            .MACRO CHECK
50                  JSR CHK           ;CHECK VARIABLE AGAINST LIMITS
51                  A1                ;ADR OF VARIABLE
52                  A2                ;MIN VALUE (POSITIVE)
53                  A3                ;MAX VALUE + 1
54                  A4                ;ADR OF ERROR TEXT STRING
55            %
56
57            .MACRO SHIFT
58                  JSR SHFT          ;SEND DATA TO CONTROL BOX
59                  A1                ;# OF BITS TO SEND
60            %
```

```
      00C2 .MAIN
01        000600  .LOC 600
02
03  00600 004533  START:  LDA 1,LBUF
04  00601 020172          LDA 0,PFINFO    ;ADR OF FINFO SECTOR
05  00602 100400          NEG 0,0
06  00603 100000          COM 0,0         ;AC0 = FINFO - 1
07  00604 040220          STA 0,TVPLOC    ;SAVE A COPY OF TVP DISK ADR
08  00605 006276          DREAD           ;READ SECTOR INTO CORE
09  00606 006273          DWAIT
10
11                        MOVE BUF+140,200,-7    ;MOVE INTO WORKING AREA
12  00607 004532          JSR .MOVE       ;MOVE A BLOCK OF CORE
13  00610 002340          BUF+140   ;FROM
14  00611 002200          200       ;TO
15  00612 177771          -7        ;- # OF WORDS TO MOVE
16  00613 102400          SUB 0,0
17  00614 040516          STA 0,EFLAG     ;CLEAR ERROR FLAG
18
19  00615 220203          LDA 0,NOF       ;CREATE WORKING VALUE OF NOF
20  00616 100400          NEG 0,0
21  00617 100000          COM 0,0
22  00620 040216          STA 0,WNOF      ;NOF -1
23
24                        CHECK ATD,0,128.,ATDTX
25  00621 004537          JSR CHK         ;CHECK VARIABLE AGAINST LIMITS
26  00622 200200          ATD       ;ADR OF VARIABLE
27  00623 000000          0         ;MIN VALUE (POSITIVE)
28  00624 000200          128.      ;MAX VALUE + 1
29  00625 001146          ATDTX     ;ADR OF ERROR TEXT STRING
30                        CHECK FFD,0,16384.,FFDTX
31  00626 004532          JSR CHK         ;CHECK VARIABLE AGAINST LIMITS
32  00627 200201          FFD       ;ADR OF VARIABLE
33  00630 000000          0         ;MIN VALUE (POSITIVE)
34  00631 040000          16384.    ;MAX VALUE + 1
35  00632 001150          FFDTX     ;ADR OF ERROR TEXT STRING
36                        CHECK FPD,1,16384.,FPDTX
37  00633 004525          JSR CHK         ;CHECK VARIABLE AGAINST LIMITS
38  00634 200202          FPD       ;ADR OF VARIABLE
39  00635 000001          1         ;MIN VALUE (POSITIVE)
40  00636 040000          16384.    ;MAX VALUE + 1
41  00637 001152          FPDTX     ;ADR OF ERROR TEXT STRING
42                        CHECK WNOF,0,4.,NOFTX
43  00640 004520          JSR CHK         ;CHECK VARIABLE AGAINST LIMITS
44  00641 200216          WNOF      ;ADR OF VARIABLE
45  00642 000000          0         ;MIN VALUE (POSITIVE)
46  00643 000004          4.        ;MAX VALUE + 1
47  00644 001154          NOFTX     ;ADR OF ERROR TEXT STRING
48                        CHECK FFI,0,16383.,FFITX
49  00645 004513          JSR CHK         ;CHECK VARIABLE AGAINST LIMITS
50  00646 200204          FFI       ;ADR OF VARIABLE
51  00647 000000          0         ;MIN VALUE (POSITIVE)
52  00650 037777          16383.    ;MAX VALUE + 1
53  00651 001156          FFITX     ;ADR OF ERROR TEXT STRING
54                        CHECK CAD,0,16384.,CADTX
55  00652 004506          JSR CHK         ;CHECK VARIABLE AGAINST LIMITS
56  00653 200205          CAD       ;ADR OF VARIABLE
57  00654 000000          0         ;MIN VALUE (POSITIVE)
58  00655 040000          16384.    ;MAX VALUE + 1
59  00656 001160          CADTX     ;ADR OF ERROR TEXT STRING
```

```
;0003 .MAIN
01
02 00657 220453 STO:    LDA 0,EFLAG     ;CHECK FOR ERRORS
03 00660 101024         MOV 0,0,SZR
04 00661 202017         ABORT           ;ERROR - ABORT EXECUTION
05
06 00662 204522         JSR SEND        ;TRANSMIT THE DATA TO THE CONTROLLER
07 00663 204521         JSR SEND        ;SEND AGAIN
08
09 00664 220206         LDA 0,MOD       ;CHECK S3
10 00665 126520         SUBZL 1,1       ;1=1
11 00666 123400         AND 1,0
12 00667 224214         LDA 1,XMOD0
13 00670 204444         JSR HCHK
14 00671 220206         LDA 0,MOD       ;CHECK S0
15 00672 101004         MOV 0,0,SZR
16 00673 102520         SUBZL 0,0       ;=1 IF MOD=1,2
17 00674 224215         LDA 1,XMOD1
18 00675 204437         JSR HCHK
19 00676 220216         LDA 0,WNOF      ;CHECK S2,S1
20 00677 224212         LDA 1,XNOF
21 00700 204434         JSR HCHK
22 00701 220200         LDA 0,ATD       ;CHECK T6 TO T0
23 00702 224207         LDA 1,XATD
24 00703 204431         JSR HCHK
25 00704 220205         LDA 0,CAD       ;CHECK D13 TO D0
26 00705 224213         LDA 1,XCAD
27 00706 204426         JSR HCHK
28 00707 220202         LDA 0,FPD       ;CHECK F13 TO F0
29 00710 224211         LDA 1,XFPD
30 00711 204423         JSR HCHK
31 00712 220201         LDA 0,FFD       ;CHECK D13 TO D0
32 00713 224210         LDA 1,XFFD
33 00714 204420         JSR HCHK
34
35 00715 220201         LDA 0,FFD       ;NOW UPDATE THE VALUE OF FFD
36 00716 224204         LDA 1,FFI       ;BY FFI
37 00717 123000         ADD 1,0
38 00720 240201         STA 0,FFD       ;NEW FFD VALUE
39                      MOVE 200,BUF+140,-7  ;RESTORE INTO BUFFER
40 00721 204420         JSR .MOVE       ;MOVE A BLOCK OF CORE
41 00722 000200         200             ;FROM
42 00723 202340         BUF+140         ;TO
43 00724 177771         -7              ;= # OF WORDS TO MOVE
44 00725 224406         LDA 1,LBUF
45 00726 220220         LDA 0,TVPLOC
46 00727 206277         DWRIT
47 00730 206273         DWAIT
48 00731 200150         EXEC            ;RETURN TO THE EXEC
49
50 00732 200000 EFLAG:  0
51 00733 202200 LBUF:   BUF
52
53
54 00734 106435 HCHK:   SUBZ# 0,1,SNR   ;AC0 = AC1 ?
55 00735 201400         JMP 0,3         ;YES, RETURN
56 00736 204511         JSR TEXT        ;NO, PRINT ERROR & ABORT
57 00737 201162         HERTX
58 00740 202017         ABORT
```

```
IM24.MAIN
01                    ;ROUTINE TO MOVE A BLOCK OF CORE FROM CALL+1
02                    ;TO CALL+2.  CALL+3 = - # OF WORDS TO MOVE.
03
04 00741 020416 MOVE: LDA 0,MOVE3         ;=3
05 00742 117000       ADD 0,3
06 00743 054413       STA 3,MOVER         ;SAVE RETURN ADDRESS
07 00744 025777       LDA 1,-1,3          ;-# OF WORDS TO MOVE
08 00745 031776       LDA 2,-3,3          ;GET SOURCE ADDRESS
09 00746 035776       LDA 3,-2,3          ;GET DESTINATION ADDRESS
10
11 00747 021000 MOVE0: LDA 0,0,2          ;MOVE A WORD
12 00750 041400       STA 0,0,3
13 00751 151400       INC 2,2             ;UPDATE THE POINTERS
14 00752 175400       INC 3,3
15 00753 125404       INC 1,1,SZR         ;COUNT A MOVE
16 00754 000773       JMP MOVE0
17 00755 002401       JMP @MOVER          ;DONE
18
19 00756 000000 MOVER: 0
20 00757 000003 MOVE3: 3
21
22                    ;ROUTINE TO CHECK A VARIABLE AGAINST ITS LIMITS
23                    ;THE ERROR FLAG 'EFLAG' WILL BE SET NON ZERO IF
24                    ;THE INPUT VARIABLE IS NEGATIVE OR NOT LESS THAN
25                    ;ITS CORESPONDING LIMIT VALUE.
26                    ;CALL+1 = ADR OF VARIABLE
27                    ;CALL+2 = LIMIT VALUE (MINIMUM - POSITIVE)
28                    ;CALL+3 = LIMIT VALUE (MAX FOR VARIABLE + 1)
29                    ;CALL+4 = ERROR TEXT STRING
30
31 00760 021403 CHK:  LDA 0,3,3           ;TEXT ADR FOR ERROR
32 00761 040417       STA 0,CHKTX         ;SAVE IT
33 00762 023400       LDA 0,0,3           ;GET ARGUMENT
34 00763 025402       LDA 1,2,3           ;MAX VALUE + 1
35 00764 031401       LDA 2,1,3           ;MINIMUM VALUE
36 00765 101132       MOVZL# 0,0,SZC      ;IS ARGUMENT POSITIVE?
37 00766 000405       JMP CHKER           ;NO, SHOW ERROR
38 00767 112032       ADCZ# 0,2,SZC       ;SKIP AC0 => AC2
39 00770 000403       JMP CHKER           ;ERROR AC0 < AC2 (MIN VAL)
40 00771 106032       ADCZ# 0,1,SZC       ;SKIP AC0 => AC1
41 00772 001404       JMP 4,3             ;AC2 <= AC0 < AC1 === O.K.
42
43 00773 054410 CHKER: STA 3,CHKR         ;SAVE RETURN ADR
44 00774 010736       ISZ EFLAG           ;SET ERROR FLAG
45 00775 004452       JSR TEXT            ;<CRLF>?<SPACE>
46 00776 001143       CRLFTX
47 00777 004450       JSR TEXT            ;PRINT ERROR STRING
48 01000 000000 CHKTX: 0
49 01001 034402       LDA 3,CHKR          ;PREPARE TO RETURN
50 01002 001404       JMP 4,3
51 01003 000000 CHKR: 0
```

```
1005 .MAIN
01
02                  ;ROUTINE TO SEND DATA VALUE TO THE CONTROLER
03                  ;
04  01004 054442 SEND:  STA 3,SENDR
05  01005 020206        LDA 0,MOD
06  01006 126520        SUBZL 1,1
07  01007 123400        AND 1,0
08                      SHIFT 1           ;SEND S3
09  01010 004470        JSR SHFT          ;SEND DATA TO CONTROL BOX
10  01011 000001        1                 ;# OF BITS TO SEND
11  01012 054214        STA 3,XMOD0       ;SAVE S3 RETURNED
12  01013 020216        LDA 0,WNDF
13                      SHIFT 2           ;SEND S2,S1
14  01014 004464        JSR SHFT          ;SEND DATA TO CONTROL BOX
15  01015 000002        2                 ;# OF BITS TO SEND
16  01016 054212        STA 3,XNDF        ;SAVE S2,S1 RETURNED
17  01017 020206        LDA 0,MOD         ;=0 OR 1 OR 2
18  01020 101024        MOV 0,0,SZR
19  01021 102520        SUBZL 0,0         ;SET = 1 IF 1 OR 2
20                      SHIFT 1           ;SEND S0
21  01022 004456        JSR SHFT          ;SEND DATA TO CONTROL BOX
22  01023 000001        1                 ;# OF BITS TO SEND
23  01024 054215        STA 3,XMOD1       ;SAVE S0 RETURNED
24  01025 020200        LDA 0,ATD
25                      SHIFT 7           ;SEND T6 TO T0
26  01026 004452        JSR SHFT          ;SEND DATA TO CONTROL BOX
27  01027 000007        7                 ;# OF BITS TO SEND
28  01030 054207        STA 3,XATD        ;SAVE RETURNED ATD
29  01031 020205        LDA 0,CAD
30                      SHIFT 14.         ;SEND P13 TO D0
31  01032 004446        JSR SHFT          ;SEND DATA TO CONTROL BOX
32  01033 000016        14.               ;# OF BITS TO SEND
33  01034 054213        STA 3,XCAD        ;SAVE RETURNED CAD
34  01035 020202        LDA 0,FPD
35                      SHIFT 14.         ;SEND P13 TO P0
36  01036 004442        JSR SHFT          ;SEND DATA TO CONTROL BOX
37  01037 000016        14.               ;# OF BITS TO SEND
38  01040 054211        STA 3,XFPD        ;SAVE RETURNED FPD
39  01041 020201        LDA 0,FFD
40                      SHIFT 14.         ;SEND P13 TO D0
41  01042 004436        JSR SHFT          ;SEND DATA TO CONTROL BOX
42  01043 000016        14.               ;# OF BITS TO SEND
43  01044 054210        STA 3,XFFD        ;SAVE RETURNED FFD
44  01045 002401        JMP @SENDR
45  01046 000000 SENDR: 0
```

```
.LOCS .MAIN
01
02 01247 021400 TEXT:   LDA 0,0,3       ;GET ADR OF STRING
03 01250 101120         MOVZL 0,0       ;MAKE INTO A BYTE POINTER
04 01251 040420         STA 0,TEXTL
05 01252 175400         INC 3,3
06 01253 054415         STA 3,TEXTR     ;SAVE RETURN ADR
07 01254 030415 TEXT0:  LDA 2,TEXTL
08 01255 151220         MOVZR 2,2
09 01256 021000         LDA 0,0,2       ;GET WORD FROM STRING
10 01257 101003         MOV 0,0,SNC
11 01260 101300         MOVS 0,0        ;USE LEFT HALF
12 01261 024411         LDA 1,TEXTM     ;BYTE MASK
13 01262 123405         AND 1,0,SNR
14 01263 002405         JMP @TEXTR      ;DONE
15 01264 006407         JSR @TEXTP      ;OUTPUT THE CHAR
16 01265 010404         ISZ TEXTL
17 01266 000766         JMP TEXT0
18 01267 000765         JMP TEXT0
19 01270 000000 TEXTR:  0
20 01271 000000 TEXTL:  0
21 01272 000377 TEXTM:  377
22 01273 001074 TEXTP:  PUT
23
24 01274 063511 PUT:    SKPBZ TTO
25 01275 000777         JMP .-1
26 01276 061111         DOAS 0,TTO
27 01277 001400         JMP 0,3
```

```
10027 .MAIN
01
02              ;ROUTINE TO SHIFT THE BITS INTO THE CONTROLLER
03              ;VALUE IN AC0, CALL +1 = # OF BITS TO SEND
04              ;RETURN IN AC3, VALUE SHIFTED FROM CONTROLLER
05
06 21100 225402 SHFT:   LDA 1,2,3        ;# OF BITS TO SEND
07 21101 175400         INC 3,3
08 21102 254433         STA 3,SHFTR      ;SAVE RETURN ADR
09 21103 244433         STA 1,SHFTC      ;USE AS A COUNTER LATER
10 21104 232433         LDA 2,SHF16      ;=16.
11 21105 176400         SUB 3,3          ;ACCUMULATE RESULT IN AC3
12 21106 146405         SUB 2,1,SNR      ;MAKE INTO A COUNTER
13 21107 300404         JMP SHFT0        ;USE AC AS IS
14
15 21110 101120 SHFT1:  MOVZL 0,0        ;LEFT JUSTIFY AC0
16 21111 125404         INC 1,1,SZR
17 21112 300776         JMP SHFT1
18
19 21113 126400 SHFT0:  SUB 1,1          ;ASSUME DATA BIT = 0
20 21114 101132         MOVZL# 0,0,SZC   ;CHECK ASSUMPTION
21 21115 324423         LDA 1,SHFTD      ;DATA = 1
22 21116 367054         DOC 1,DIM        ;SET DATA LINE
23 21117 230422         LDA 2,SHFTS      ;STROBE BIT PATTERN
24 21120 147400         ADD 2,1
25 21121 367054         DOC 1,DIM        ;SET STROBE BIT ON
26 21122 224416         LDA 1,SHFTD      ;SET DATA BIT=1 TO ENABLE TKS HARDWARE
27 21123 367054         DOC 1,DIM        ;CLEAR DATA & STROBE LINES
28 21124 101100         MOVL 0,0         ;SHIFT DATA WORD LEFT
29 21125 371454         DIB 2,DIM        ;READ SENSE REGISTER
30 21126 224414         LDA 1,SHFIN      ;MASK FOR INPUT BIT
31 21127 133415         AND# 1,2,SNR
32 21130 175121         MOVZL 3,3,SKP    ;BIT=0
33 21131 175140         MOVOL 3,3        ;BIT=1
34 21132 314404         DSZ SHFTC        ;COUNT BITS PROCESSED
35 21133 300767         JMP SHFT0        ;MORE TO DO
36 21134 302401         JMP @SHFTR       ;DONE, EXIT
37
38 21135 000000 SHFTR:  0
39 21136 000000 SHFTC:  0
40 21137 000020 SHF16:  16.
41 21140 020000 SHFTD:  DATA
42 21141 010000 SHFTS:  STROBE
43 21142 000000 SHFIN:  SENSE
```

```
.TITL .MAIN
01
02      200001 .TXTM 1
03
04 01143 306412 CRLFTX: .TXT "<15><12>? "
05        237442
06        200000
07 01146 240524 ATDTX:  .TXT "ATD"
08        212002
09 01150 243106 FFDTX:  .TXT "FFD"
10        242002
11 01152 243120 FPDTX:  .TXT "FPD"
12        242002
13 01154 247117 NOFTX:  .TXT "NOF"
14        243002
15 01156 243106 FFITX:  .TXT "FFI"
16        244402
17 01160 341501 CADTX:  .TXT "CAD"
18        242002
19 01162 306412 HERTX:  .TXT "<15><12>CONTROLLER FAILURE<15><12>"
20        341517
21        347124
22        351117
23        246114
24        242522
25        200106
26        246511
27        246125
28        251105
29        306412
30        200002
31
32      201176 FOO=.
33        .END

**00000 TOTAL ERRORS, 00000 PASS 1 ERRORS
```

.0009 .MAIN

| | | | | | | | | |
|---|---|---|---|---|---|---|---|---|
| ABORT | 002317 | | 1/15 | 3/04 | 3/58 | | | |
| ATD | 000200 | | 1/23 | 2/26 | 3/22 | 5/24 | | |
| ATDTX | 001146 | | 2/29 | 8/07 | | | | |
| BUF | 022200 | | 1/12 | 2/13 | 3/42 | 3/51 | | |
| CAD | 000205 | | 1/28 | 2/56 | 3/25 | 5/29 | | |
| CADTX | 001160 | | 2/59 | 8/17 | | | | |
| CHECK | 000212 | MC | 1/49 | 2/24 | 2/30 | 2/36 | 2/42 | 2/48 | 2/54 |
| CHK | 000766 | | 2/25 | 2/31 | 2/37 | 2/43 | 2/49 | 2/55 | 4/31 |
| CHKER | 000773 | | 4/37 | 4/39 | 4/43 | | | |
| CHKR | 001203 | | 4/43 | 4/49 | 4/51 | | | |
| CHKTX | 001200 | | 4/32 | 4/48 | | | | |
| CRLFT | 001143 | | 4/46 | 8/04 | | | | |
| DATA | 020300 | | 1/08 | 7/41 | | | | |
| DREAD | 006276 | | 1/17 | 2/08 | | | | |
| DWAIT | 006273 | | 1/19 | 2/09 | 3/47 | | | |
| DWRIT | 006277 | | 1/18 | 3/46 | | | | |
| EFLAG | 000732 | | 2/17 | 3/22 | 3/50 | 4/44 | | |
| EXEC | 000150 | | 1/14 | 3/48 | | | | |
| FFD | 000201 | | 1/24 | 2/32 | 3/31 | 3/35 | 3/38 | 5/39 |
| FFDTX | 001150 | | 2/35 | 8/09 | | | | |
| FFI | 000204 | | 1/27 | 2/50 | 3/36 | | | |
| FFITX | 001156 | | 2/53 | 8/15 | | | | |
| FOO | 001176 | | 8/32 | | | | | |
| FPD | 000202 | | 1/25 | 2/38 | 3/28 | 5/34 | | |
| FPDTX | 001152 | | 2/41 | 8/11 | | | | |
| HCHK | 000734 | | 3/13 | 3/18 | 3/21 | 3/24 | 3/27 | 3/30 | 3/33 |
| | | | 3/54 | | | | | |
| HERTX | 001162 | | 3/57 | 8/19 | | | | |
| LEUF | 000733 | | 2/03 | 3/44 | 3/51 | | | |
| MOD | 000206 | | 1/29 | 3/09 | 3/14 | 5/05 | 5/17 | |
| MOVE | 000300 | MC | 1/42 | 2/11 | 3/39 | | | |
| MOVE0 | 000747 | | 4/11 | 4/16 | | | | |
| MOVE3 | 000757 | | 4/04 | 4/20 | | | | |
| MOVER | 000756 | | 4/06 | 4/17 | 4/19 | | | |
| NOF | 000203 | | 1/26 | 2/19 | | | | |
| NOFTX | 001154 | | 2/47 | 8/13 | | | | |
| PRINF | 000172 | | 1/21 | 2/04 | | | | |
| PUT | 001074 | | 6/22 | 6/24 | | | | |
| SEND | 001204 | | 3/06 | 3/07 | 5/04 | | | |
| SENDR | 001046 | | 5/04 | 5/44 | 5/45 | | | |
| SENSE | 020200 | | 1/10 | 7/43 | | | | |
| SHF16 | 001137 | | 7/10 | 7/40 | | | | |
| SHFT | 001100 | | 5/09 | 5/14 | 5/21 | 5/26 | 5/31 | 5/36 | 5/41 |
| | | | 7/06 | | | | | |
| SHFT0 | 001113 | | 7/13 | 7/19 | 7/35 | | | |
| SHFT1 | 001110 | | 7/15 | 7/17 | | | | |
| SHFTC | 001136 | | 7/09 | 7/34 | 7/39 | | | |
| SHFTD | 001140 | | 7/21 | 7/26 | 7/41 | | | |
| SHFTN | 001142 | | 7/30 | 7/43 | | | | |
| SHFTR | 001135 | | 7/08 | 7/36 | 7/38 | | | |
| SHFTS | 001141 | | 7/23 | 7/42 | | | | |
| SHIFT | 000333 | MC | 1/57 | 5/08 | 5/13 | 5/20 | 5/25 | 5/30 | 5/35 |
| | | | 5/40 | | | | | |
| STA | 000657 | | 3/02 | | | | | |
| START | 000600 | | 2/03 | | | | | |
| STROB | 010300 | | 1/09 | 7/42 | | | | |
| TEXT | 001247 | | 3/56 | 4/45 | 4/47 | 6/02 | | |
| TEXT0 | 001254 | | 6/07 | 6/17 | 6/18 | | | |
| TEXTL | 001271 | | 6/04 | 6/07 | 6/16 | 6/20 | | |

P013 .MAIN

| | | | | | |
|---|---|---|---|---|---|
| TEXTM | 001272 | 6/12 | 6/21 | | |
| TEXTP | 001273 | 6/15 | 6/22 | | |
| TEXTR | 001270 | 6/06 | 6/14 | 6/19 | |
| TYPLO | 000220 | 1/40 | 2/07 | 3/45 | |
| WNOF | 000216 | 1/38 | 2/22 | 2/44 | 3/19 5/12 |
| XATD | 000207 | 1/31 | 3/23 | 5/28 | |
| XCAD | 000213 | 1/35 | 3/26 | 5/33 | |
| XFFD | 000210 | 1/32 | 3/32 | 5/43 | |
| XFPD | 000211 | 1/33 | 3/29 | 5/38 | |
| XMOD0 | 000214 | 1/36 | 3/12 | 5/11 | |
| XMOD1 | 000215 | 1/37 | 3/17 | 5/23 | |
| XNOF | 000212 | 1/34 | 3/20 | 5/16 | |
| .MOVE | 000741 | 2/12 | 3/40 | 4/04 | |

```
CP01  MAIN MACRO REV 04.00              15:05:47 01/13/77
01              ;PROGRAM TKS - TIME - KINETIC - STUDIES
02              ;FIRST SECTOR AT 207
03              ;
04              ;11/16/76 - RCS
05              ;
06    000207    PROG=207
07    002600    OBUF=2600
08    004600    IBUF=OBUF+1024.
09    006600    ITAB=IBUF+1024.
10    010600    OTAB=ITAB+1024.
11    012600    STAB=OTAB+1024.
12    014600    DKTAB=STAB+1024.
13    016600    FBUF=DKTAB+1024.
14
15    000150    EXEC=JMP 150
16    002017    ABORT=JMP @17
17    000276    READ=276
18    000277    WRITE=277
19    006276    DREAD=JSR @READ   ;DISK READ (AC0=SECTOR, AC1=CORE)
20    006277    DWRIT=JSR @WRITE  ;DISK WRITE (DITTO)
21    006273    DWAIT=JSR @273    ;DISK WAIT
22
23    000376    KESC=376          ;ADR FOR SYSTEM ESCAPE CHAR
24    000172    PFINFO=172
25    000065    FLD=65
26    000112    FLS=112
27    000137    CNT=137
28    000145    FINCT=145
29    000176    KPGM=176
30    000166    DMAX=166
31
32    000146    AMOD=146          ;DISP FOR MOD INTO TVP
33
34    000200    TVPLOC=200
35    000201    MOD=TVPLOC+1
36    000202    IPTR=TVPLOC+2     ;POINTER FOR BUFFER INPUT TABLE
37    000203    OPTR=TVPLOC+3     ;POINTER FOR BUFFER OUTPUT TABLE
38    000204    PNTS=TVPLOC+4     ;# OF POINTS (D.P.)
39    000206    DISP=TVPLOC+6     ;TEMP AND INPUT DISPLACEMENT
40    000207    FILE=TVPLOC+7
41    000210    KNT=TVPLOC+10
42    000211    GFW=TVPLOC+11     ;FIRST WORD IN FINFO BLOCK
43    000212    NSCN=TVPLOC+12    ;2ND
44    000213    NSEC=TVPLOC+13    ;# OF INPUT SECTORS
45    000214    SPTR=TVPLOC+14    ;POINTER TO SCALE TABLE
46    000215    PEAK=TVPLOC+15    ;LOCATION OF PEAK VALUE
47    000216    SCAL=TVPLOC+16
48    000217    OFILE=TVPLOC+17
49    000220    IDELT=TVPLOC+20
50    000221    ODELT=TVPLOC+21
51    000222    ONSEC=TVPLOC+22   ;# OF SECTORS IN OUTPUT FILE
52    000223    TCNT=TVPLOC+23    ;FUNNY CNT VALUE
53    000224    IDSP=TVPLOC+24
54    000225    ODSP=TVPLOC+25
55    000226    PRFLD=TVPLOC+26
56    000227    SOFILE=TVPLOC+27  ;SAVED OFILE
57    000230    FST=TVPLOC+30     ;FLS STARTING ADDRESS
58    000231    TSECT=TVPLOC+31   ;TOTAL SECTOR LENGTH (FLS)
59    000232    TRSEC=TVPLOC+32   ;TOTAL ROUNDED LENGTH (FLD)
60    000233    DPE=TVPLOC+33
```

```
.ROOT .MAIN
01    200234 RES=TVPLOC+34
02    200235 PTZ=TVPLOC+35
03    200236 TSCAT=TVPLOC+36
04    200237 SECL=TVPLOC+37   ;ROUNDED FLD LENGTH
05
06    200240 LIBUF=TVPLOC+40 ;POINTER TO INPUT BUFFER
07    200241 LOBUF=LIBUF+1   ;POINTER TO OUTPUT BUFFER
08    200242 LSTAB=LIBUF+2
09    200243 LOKTAB=LIBUF+3
10    200244 LFBUF=LIBUF+4
11    200245 FGET=LIBUF+5
12    200246 DIVIDE=LIBUF+6
13    200247 FPROS=LIBUF+7
14    200250 FFIX=LIBUF+10
15    200251 K377=LIBUF+11
16    200252 K1774K=LIBUF+12
17    200253 K40K=LIBUF+13
18    200254 LITAB=LIBUF+14
19    200255 LOTAB=LIBUF+15
20    200256 K177=LIBUF+16
21    200257 MULT=LIBUF+17
22    200260 ICHK=LIBUF+20
23    200261 K400=LIBUF+21
24    200262 BUFI=LIBUF+22
25    200263 XTFILL=LIBUF+23
26    200264 MASKR=LIBUF+24
27    200265 MASKL=LIBUF+25
28    200266 K4=LIBUF+26
```

```
LEV23.MAIN
01
02      200600  .LOC 600
03
04 00600 260210 START: NIOC TTI          ;CLEAR TTI
05 00601 320427        LDA 0,NEXTA       ;PREPARE TO LOAD IN REST OF PROGRAM
06 00602 340442        STA 0,NXTC
07 00603 320432        LDA 0,NEXTB
08 00604 340441        STA 0,NXTS
09 00605 226437 ST0:   LDA 1,@NXTC       ;CORE ADR
10 00606 125005        MOV 1,1,SNR
11 00607 200427        JMP ST0B          ;DONE
12 00610 222435        LDA 0,@NXTS       ;DISK SECTOR ADR
13 00611 206276        DREAD
14 00612 206273        DWAIT
15 00613 210431        ISZ NXTC
16 00614 210431        ISZ NXTS
17 00615 000770        JMP ST0
18
19 00616 234423 ST0B:  LDA 3,NEXTC       ;SETUP PAGE 0 LOCATIONS
20 00617 230423        LDA 2,NEXTD
21 00620 024423        LDA 1,NEXTE
22 00621 221400 ST0A:  LDA 0,0,3
23 00622 041000        STA 0,0,2
24 00623 151400        INC 2,2
25 00624 175400        INC 3,3
26 00625 125404        INC 1,1,SZR
27 00626 000773        JMP ST0A
28 00627 000425        JMP ST1
29
30 00630 200631 NEXTA: .+1
31 00631 201200        1200
32 00632 201600        1600
33 00633 202200        2200
34 00634 000000        0
35 00635 000636 NEXTB: .+1
36 00636 200210        PROG+1
37 00637 200211        PROG+2
38 00640 200212        PROG+3
39 00641 002510 NEXTC: NEXTP
40 00642 000240 NEXTD: LIBUF
41 00643 177751 NEXTE: NEXTP-FOO         ;-# OF WORDS TO MOVE
42 00644 000000 NXTC:  0
43 00645 000000 NXTS:  0
44
45 00646 003777 K3777: 3777
46
47 00647 201143 ATE1:  STE1
48 00650 201145 ATE2:  STE2
49 00651 201153 ATE6:  STE6
50 00652 201155 ATE7:  STE7
51 00653 201163 ATE11: STE11
```

```
.RDCM .MAIN
C1
C2  00654 226172 ST1:    LDA 0,PFINFO      ;FINFO ADR
C3  00655 240200         STA 0,TVPLOC
C4  00656 014200         DSZ TVPLOC
C5  00657 020200         LDA 0,TVPLOC
C6  00660 224240         LDA 1,LIBUF
C7  00661 006276         DREAD
C8  00662 006273         DWAIT
C9  00663 230240         LDA 2,LIBUF
10  00664 021146         LDA 0,AMOD,2      ;GET VALUE OF MOD
11  00665 240201         STA 0,MOD
12
13  00666 024137         LDA 1,CNT
14  00667 127057         ADDO# 1,1,SBN     ;SKIP CNT >0
15  00670 000760         JMP @ATE2         ;CNT ERROR
16  00671 044210         STA 1,KNT
17  00672 044532         STA 1,ST4D2
18  00673 101005         MOV 0,0,SNR
19  00674 000405         JMP ST1A          ;MOD=0=KS
20  00675 126520         SUBZL 1,1         ;=1
21  00676 131100         MOVZL 1,2         ;=2
22  00677 101232         MOVZR# 0,0,SZC    ;SKIP MOD=2=TR
23  00700 147000         ADD 2,1           ;MOD=1=TK
24  00701 044223 ST1A:   STA 1,TCNT
25  00702 044510         STA 1,ST4D0
26
27  00703 020112         LDA 0,FLS
28  00704 040207         STA 0,FILE
29  00705 006245         JSR @FGET
30  00706 000741         JMP @ATE1         ;FLS ERROR
31  00707 021000         LDA 0,0,2         ;1ST FINFO WORD FOR ENTRY
32  00710 040211         STA 0,GFW
33  00711 025001         LDA 1,1,2         ;2ND WORD
34  00712 044212         STA 1,NSCN
35  00713 024733         LDA 1,K3777
36  00714 107405         AND 0,1,SNR
37  00715 000736         JMP @ATE11        ;FINFO ERROR
38  00716 044213         STA 1,NSEC
39  00717 025002         LDA 1,2,2         ;3RD WORD = SCALINGS
40  00720 044216         STA 1,SCAL        ;USE A INITIAL VALUE
41  00721 024253         LDA 1,K40K
42  00722 030261         LDA 2,K400
43  00723 107404         AND 0,1,SZR
44  00724 151200         MOVZR 2,2         ;FILE IS DP
45  00725 044233         STA 1,DPF         ;SAVE FLAG
46  00726 153120         ADDZL 2,2         ;4X
47  00727 050235         STA 2,PTZ         ;# OF POINTS/BLOCK (BLK=4 SECTORS)
48  00730 050465         STA 2,ST4D1
49
50  00731 020213         LDA 0,NSEC        ;CHECK FOR LEGAL FILE SIZE
51  00732 006260         JSR @ICHK
52  00733 000720         JMP @ATE11        ;NOT A POWER OF 2
53  00734 020213         LDA 0,NSEC
54  00735 101220         MOVZR 0,0
55  00736 101225         MOVZR 0,0,SNR
56  00737 000714         JMP @ATE11        ;FILE TOO SMALL
57
58  00740 020242         LDA 0,LSTAR       ;ADR OF SCALINGS TABLE
59  00741 040214         STA 0,SPTR        ;USE AS POINTER
```

```
15705 .MAIN
01
02  00742 220207 ST2:    LDA 0,FILE         ;GET INPUT SCALINGS FOR ALL FILES
03  00743 206245         JSR @FGET          ;AND PUT INTO STAB
04  00744 000705         JMP @ATE6          ;FILE NOT IN FINFO
05  00745 021000         LDA 0,0,2
06  00746 024211         LDA 1,GFW
07  00747 106434         SUBZ# 0,1,SZP
08  00750 000702         JMP @ATE7          ;FILES DIFFER - SIZE, TYPE
09  00751 021002         LDA 0,2,2          ;GET # OF SCALINGS
10  00752 042214         STA 0,@SPTR
11  00753 010214         ISZ SPTR
12  00754 010207         ISZ FILE
13  00755 014210         DSZ KNT
14  00756 000764         JMP ST2
15
16  00757 020223         LDA 0,TCNT
17  00760 040210         STA 0,KNT
18  00761 020065         LDA 0,FLD
19  00762 040207         STA 0,FILE
20
21  00763 020207 ST3:    LDA 0,FILE
22  00764 006245         JSR @FGET
23  00765 000562         JMP STE3           ;FLD ERROR
24  00766 010207         ISZ FILE
25  00767 014210         DSZ KNT
26  00770 000773         JMP ST3
27
28  00771 020213         LDA 0,NSEC
29  00772 024137         LDA 1,CNT
30  00773 006257         JSR @MULT          ;SLOW MULTIPLY AC0,1=AC0*AC1
31  00774 101004         MOV 0,0,SZR
32  00775 000570         JMP STE12          ;SOMETHING WRONG!!
33  00776 044231         STA 1,TSECT        ;# OF SECTOS OF INPUT
34  00777 030261         LDA 2,K400         ;=256.
35  01000 034233         LDA 3,DPF
36  01001 175004         MOV 3,3,SZR
37  01002 151220         MOVZR 2,2          ;ONLY 128. IN A DP SECTOR
38  01003 151220         MOVZR 2,2          ;CORRECT FOR COUNTING
39  01004 125120 ST4:    MOVZL 1,1          ;DP. LEFT SHIFT
40  01005 101100         MOVL 0,0
41  01006 151224         MOVZR 2,2,SZR      ;COUNT BY SHIFTING
42  01007 000775         JMP ST4
43
44  01010 006246         JSR @DIVIDE        ;AC0,1=TOTAL # OF INPUT POINTS
45  01011 000000         0
46  01012 000000 ST4D0:  0                  ;DIVIDE BY TCNT = CNT,3,1
47
48  01013 006246         JSR @DIVIDE
49  01014 000000         0
50  01015 000000 ST4D1:  0                  ;(=PTZ=128. OR =256.)*4
```

```
12026 .MAIN
01
02 01016 244222        STA 1,ONSEC      ;# OF WHOLE OUTPUT BLOCKS/FILE
03 01017 244237        STA 1,SECL
04 01020 165000        MOV 3,1          ;AC1 = REMAINDER (POINTS)
05 01021 102400        SUB 0,0          ;FAKE A DP NUMBER
06 01022 006246        JSR @DIVIDE
07 01023 000000        0
08 01024 000000 STAD2: 0                ;CNT
09 01025 244234        STA 1,RES        ;# OF RESIDUAL POINTS/INPUT FILE
10 01026 125404        MOV 1,1,SZR
11 01027 010237        ISZ SECL         ;SHOW EXISTANCE OF PARTIAL SECTOR
12
13 01030 020237        LDA 0,SECL       ;NOW CHECK FOR LEGAL FILE SIZE
14 01031 103120        ADDZL 0,0        ;4X = # OF SECTORS
15 01032 040237        STA 0,SECL
16 01033 040236        STA 0,TSDAT      ;# OF OUTPUT (ROUNDED) DATA SECTORS
17 01034 006260        JSR @ICHK
18 01035 050237        STA 2,SECL       ;ROUND TOTAL SECTOR COUNT UP
19
20 01036 020237        LDA 0,SECL       ;LENGTH OF OUPUT FILE
21 01037 024223        LDA 1,TCNT       ;# OF OUTPUT FILES
22 01040 006257        JSR @MULT        ;COMPUTE LENGTH (TOTAL) OF OUPUT AREA
23 01041 101004        MOV 0,0,SZR      ;SHOULDN'T OVERFLOW INTO MSH
24 01042 000523        JMP STE12        ;FLD*TCNT OVERFLOWED!
25 01043 044232        STA 1,TRSEC      ;SAVE OUTPUT AREA SIZE
26
27 01044 020137        LDA 0,CNT        ;CHECK FOR CNT TOO BIG
28 01045 024235        LDA 1,PTZ        ;# OF POINTS/BLOCK = MAX CNT VAL
29 01046 106433        SUBZ# 0,1,SNC    ;SKIP AC0 <= AC1
30 01047 000476        JMP STE2         ;ERROR - CNT TOO BIG
31
32 01050 024137        LDA 1,CNT        ;# OF INPUT FILES
33 01051 020234        LDA 0,RES        ;# OF RESIDUAL POINTS/INPUT FILE
34 01052 006257        JSR @MULT
35 01053 040204        STA 0,PNTS       ;SAVE # OF POINTS IN PARTIAL
36 01054 044205        STA 1,PNTS+1
37 01055 024222        LDA 1,ONSEC      ;# OF WHOLE OUTPUT BLOCKS
38 01056 020235        LDA 0,PTZ        ;# OF POINTS/BLOCK
39 01057 006257        JSR @MULT        ;# OF POINTS/WHOLE SECTION
40 01060 030204        LDA 2,PNTS       ;RETRIEVE # OF PARTIAL POINTS
41 01061 034205        LDA 3,PNTS+1
42 01062 167022        ADDZ 3,1,SZC     ;DP ADD
43 01063 101400        INC 0,0
44 01064 143000        ADD 2,0
45 01065 040204        STA 0,PNTS       ;# OF POINTS IN OUTPUT FILE
46 01066 044205        STA 1,PNTS+1
```

```
12327 .MAIN
21
02 01267 204432 ST7:    JSR ACAL        ;CHECK DISK ADRS FOR OVERLAP
03 01272 000112         FLS
04 01271 000213         NSEC
05 01272 000231         TSECT           ;TOTAL INPUT AREA SIZE
06 01273 000464         JMP STE8        ;FLS>DMAX
07
08 01274 040230         STA 0,FST       ;FLS START DISK ADR
09 01275 044423         STA 1,FND       ;FLS END +1 DISK ADR
10
11 01276 004423         JSR ACAL
12 01277 000065         FLD
13 01300 000237         SECL
14 01301 000232         TRSEC           ;TOTAL OUTPUT AREA SIZE
15 01302 000457         JMP STE9        ;FLD>DMAX
16
17 01303 040217         STA 0,OFILE     ;SAVE DISK FLD ADDRESS (INITIAL)
18
19 01304 032230         LDA 2,FST       ;AC0=FLD START ADR
20 01305 034413         LDA 3,FND       ;AC1=FLD END +1 ADR
21
22 01306 112435         SUBZ# 0,2,SNR   ;SKIP IF FLS<>FLD
23 01307 000442         JMP STE5        ;START FLS=FLD (OVERLAP)
24 01310 142432         SUBZ# 2,0,SZC   ;SKIP START FLS > FLD
25 01311 000404         JMP .+4         ;START FLD > FLS
26 01312 146032         ADCZ# 2,1,SZC   ;SKIP IF FLS => FLD (END+1)
27 01313 000436         JMP STE5        ;OVERLAP
28 01314 000512         JMP SCALE       ;OK
29 01315 116032         ADCZ# 0,3,SZC   ;SKIP IF FLD => FLS (END+1)
30 01316 000433         JMP STE5        ;OVERLAP
31 01317 000507         JMP SCALE       ;CALCULATE SCALINGS
32
33 01320 000000 FND:    0
34
35 01321 027401 ACAL:   LDA #1,1,3      ;# OF SECTORS
36 01322 033400         LDA #2,0,3      ;FILE #
37 01323 102400         SUB 0,0
38 01324 152405         NEG 2,2,SNR     ;CONVER FILE # INTO A COUNTER
39 01325 000404         JMP ACAL0       ;FILE # = 0
40 01326 123000 ACAL1:  ADD 1,0         ;COMPUTE DISP INTO FREE AREA
41 01327 151404         INC 2,2,SZR
42 01330 000776         JMP ACAL1
43 01331 030176 ACAL0:  LDA 2,KPGM      ;=ADR OF START OF FREE AREA
44 01332 143000         ADD 2,0         ;AC0 = STARTING DISK ADR
45 01333 030166         LDA 2,DMAX      ;END OF DISK AREA
46 01334 112033         ADCZ# 0,2,SNC   ;SKIP IF ADR < DMAX
47 01335 001403         JMP 3,3         ;ERROR ADR (START) => DMAX
48 01336 027402         LDA #1,2,3      ;AC1=# OF SECTORS (TOT) IN FLS,FLD
49 01337 107000         ADD 0,1         ;AC1=END+1 DISK ADR
50 01340 132433         SUBZ# 1,2,SNC   ;SKIP IF END ADR <= DMAX
51 01341 001403         JMP 3,3         ;ERROR ADR (END) > DMAX
52 01342 001404         JMP 4,3         ;TAKE GOOD RETURN
```

```
18008 .MAIN
01
02 01143 204124 STE1:   JSR EPR  ;FLS ERROR
03 01144 002366         FLSTX
04 01145 004122 STE2:   JSR EPR  ;CNT ERROR
05 01146 002373         CNTTX
06 01147 004420 STE3:   JSR EPR  ;FLD ERROR
07 01150 002400         FLDTX
08 01151 004416 STE5:   JSR EPR  ;FLS,FLD OVERLAP
09 01152 002405         FLOTX
10 01153 004414 STE6:   JSR EPR  ;FLS,FLD NOT IN FINFO
11 01154 002415         FINTX
12 01155 004412 STE7:   JSR EPR  ;INPUT FILES DIFFER
13 01156 002425         FSTTX
14 01157 004410 STE8:   JSR EPR  ;FLS TOO BIG FOR DISK
15 01160 002442         FSTBTX
16 01161 004406 STE9:   JSR EPR  ;FLD TOO BIG FOR DISK
17 01162 002451         FDTBTX
18 01163 004404 STE11:  JSR EPR  ;FINFO ENTRY ERROR
19 01164 002460         FETX
20 01165 004402 STE12:  JSR EPR  ;CNT*FLS,FLD LENGTH > 32767
21 01166 002471         CNFSX
22
23 01167 021400 EPR:    LDA 0,0,3        ;GET STRING ADR
24 01170 040404         STA 0,EPRL
25 01171 004405         JSR TEXT         ;PRINT CRLF ?
26 01172 002363         CRETX
27 01173 004403         JSR TEXT         ;PRINT ERROR STRING
28 01174 000000 EPRL:   0
29 01175 002017         ABORT            ;ABORT THE PROGRAM
30
31 01176 021400 TEXT:   LDA 0,0,3        ;GET STRING ADR
32 01177 101120         MOVZL 0,0        ;MAKE INTO A BYTE POINTER
33 01200 040421         STA 0,TEXTL      ;SAVE IT
34 01201 175400         INC 3,3
35 01202 054415         STA 3,TEXTR
36 01203 024251         LDA 1,K377
37 01204 030415 TEXT0:  LDA 2,TEXTL
38 01205 151220         MOVZR 2,2
39 01206 021000         LDA 0,0,2
40 01207 101003         MOV 0,0,SNC
41 01210 101300         MOVS 0,0
42 01211 123405         AND 1,2,SNR
43 01212 002405         JMP *TEXTR       ;DONE WITH STRING
44 01213 006405         JSR *TEXTP       ;PRINT CHAR
45 01214 010405         ISZ TEXTL
46 01215 000767         JMP TEXT0
47 01216 000766         JMP TEXT0
48 01217 000000 TEXTR:  0
49 01220 001222 TEXTP:  PUT
50 01221 000000 TEXTL:  0
51
52 01222 063511 PUT:    SKPBZ TTO
53 01223 000777         JMP .-1
54 01224 061111         DOAS 0,TTO
55 01225 001400         JMP 0,3
```

```
10039 .MAIN
01  21226 020137 SCALE:  LDA 0,CNT
02  21227 040210         STA 0,KNT       ;LOOP COUNTER
03  21230 020242         LDA 0,LSTAR     ;ADR OF STAR (SCALINGS)
04  21231 040214         STA 0,SPTR
05
06  21232 024216         LDA 1,SCAL      ;ASSUMED SCAL MIN VALUE
07  21233 022214 SC0:    LDA 0,@SPTR     ;FIND SMALLEST SCALE FACTOR
08  21234 106113         ADCL# 0,1,SNC   ;SIGNED SKIP IF AC0 >= AC1
09  21235 105000         MOV 0,1         ;AC0 < AC1 UPDATE AC1
10  21236 010214         ISZ SPTR        ;POINT TO NEXT ENTRY
11  21237 014210         DSZ KNT
12  21240 000773         JMP SC0
13  21241 044216         STA 1,SCAL      ;SMALLEST SCALE FACTOR
14
15  21242 004443 SC1:    JSR PR          ;PROCESS THE FILES
16  21243 000150         EXEC            ;RETURN TO ETS SYSTEM
17
18                       ;ROUTINE TO SEE IF THE # IN AC0 IS =2**N
19                       ;RETURN TO CALL+1 IF <>2**N
20                       ;TO CALL+2 IF = 2**N
21                       ;ON RETURN AC2=POWER OF 2 ROUNDED UP
22
23  21244 054417 ICHKX:  STA 3,ICHKR
24  21245 176620         SUBZR 3,3       ;=100000
25  21246 152520         SUBZL 2,2       ;=1
26  21247 101005         MOV 0,0,SNR     ;AC0=0?
27  21250 002413         JMP @ICHKR      ;SHOW AS AN ERROR
28  21251 175220 ICHK0:  MOVZR 3,3       ;SEARCH FOR MSB
29  21252 117415         AND# 0,3,SNR
30  21253 000776         JMP ICHK0
31  21254 171000         MOV 3,2         ;SAVE A COPY OF THE POWER MASK
32  21255 116000         ADC 0,3         ;AC3=-1 IF AC0=2**N
33  21256 175415         INC# 3,3,SNR
34  21257 010404         ISZ ICHKR       ;=2**N
35  21260 175414         INC# 3,3,SZR
36  21261 151120         MOVZL 2,2       ;ROUND UP, AC0<>2**N
37  21262 002401         JMP @ICHKR
38  21263 000000 ICHKR:  0
39
40                       ;ROUTINE TO MULTIPLY AC0 BY AC1
41                       ;#'S ARE ASSUMMED POSITIVE
42                       ;RESULT IN AC0,1 (THE LONG WAY)
43
44  21264 054417 MULX:   STA 3,MULXR
45  21265 050417         STA 2,MULX2
46  21266 152400         SUB 2,2
47  21267 176400         SUB 3,3
48  21270 101004         MOV 0,0,SZR     ;SKIP IF AC0=0=NULL RESULT
49  21271 124405         NEG 1,1,SNR     ;MAKE INTO A COUNTER
50  21272 000405         JMP MULX1       ;#=0
51  21273 117022 MULX0:  ADDZ 0,3,SZC    ;PARTIAL DP. ADD
52  21274 151400         INC 2,2
53  21275 125404         INC 1,1,SZR
54  21276 000775         JMP MULX0
55  21277 165000 MULX1:  MOV 3,1
56  21300 141000         MOV 2,0
57  21301 030403         LDA 2,MULX2
58  21302 002401         JMP @MULXR
59  21303 000000 MULXR:  0
60  21304 000000 MULX2:  0
```

```
.MAIN
01
02          ;ROUTINE TO PROCESS THE INPUT FILES INTO THE
03          ;OUTPUT FILES.
04
05 01305 254513  PR:    STA 3,PRP      ;SAVE RETURN ADR
06 01306 224265         LDA 1,FLD
07 01307 244226         STA 1,PRFLD    ;OUTPUT FILE #
08 01310 224137         LDA 1,CNT      ;CALCULATE TABLE DELTAS
09 01311 034233         LDA 3,DPF
10 01312 175004         MOV 3,3,SZR
11 01313 125120         MOVZL 1,1      ;FILE IS DP
12 01314 244221         STA 1,ODELT    ;OUTPUT DELTA VALUE
13
14 01315 020223         LDA 0,TCNT
15 01316 040503         STA 0,PROFN    ;# OF OUTPUT FILES
16 01317 175204         MOV 3,3,SZR    ;CHECK FILE TYPE
17 01320 101120         MOVZL 0,0      ;IS D.P.
18 01321 040220         STA 0,IDELT
19
20 01322 020137         LDA 0,CNT
21 01323 024201         LDA 1,MOD
22 01324 125004         MOV 1,1,SZR
23 01325 102400         SUB 0,0
24 01326 040206         STA 0,DISP     ;=CNT IF MOD=0=KS, ELSE =0
25
26 01327 152520         SUBZL 2,2      ;=1, CALCULATE ITAB,OTAB OFFSET
27 01330 050225         STA 2,ODSP     ;=1
28 01331 125004         MOV 1,1,SZR    ;SKIP IF MOD=KS
29 01332 152400         SUB 2,2        ;MOD=TR,TK
30 01333 050224         STA 2,IDSP     ;=0,1
31
32
33 01334 020217  PR2:   LDA 0,OFILE    ;INITIALLY =SOFILE
34 01335 040207         STA 0,SOFILE   ;USED WITH MULTIPLE OUTPUT FILES
35
36 01336 006263         JSR @XTFILL    ;FILL ITAB
37 01337 006600         ITAB
38 01340 000224         IDSP
39
40 01341 006263         JSR @XTFILL    ;FILL OTAB
41 01342 010600         OTAB
42 01343 000225         ODSP
43
44 01344 020137         LDA 0,CNT
45 01345 040210         STA 0,KNT
46 01346 020230         LDA 0,FST      ;ADDRESS OF FIRST FLS FILE
47 01347 024213         LDA 1,NSEC     ;#OF SECTORS/FILE (INPUT)
48 01350 030243         LDA 2,LOKTAB   ;ADR OF CKTAB
```

```
1/011 .MAIN
01
02  01351  241002  PR2C:   STA 0,0,2           ;BUILD CKTAB (DISK ADRS)
03  01352  151400          INC 2,2
04  01353  123000          ADD 1,0
05  01354  014210          DSZ KNT
06  01355  000774          JMP PR2C
07  01356  006262          JSR @BUFI           ;INIT BUFFER
08
09  01357  020202          LDA 0,ONSEC
10  01360  024137          LDA 1,CNT           ;# OF INPUT FILES
11  01361  004446          JSR PR.             ;PROCESS WHOLE SECTORS
12
13  01362  102520          SUBZL 0,0
14  01363  024234          LDA 1,RES           ;# OF POINTS/FILE (PARTIAL SECTOR)
15  01364  125004          MOV 1,1,SZR
16  01365  004440          JSR PRX.            ;PROCESS PARTIAL SECTOR
17
18  01366  024236          LDA 1,TSDAT         ;NEED TO ZERO FILL?
19  01367  020237          LDA 0,SECL          ;# OF OUTPUT SECTORS
20  01370  122405          SUB 1,0,SNR         ;=# OF SECTORS OF FILLING
21  01371  000412          JMP PR0C            ;NO FILLING
22  01372  040210          STA 0,KNT
23  01373  006262          JSR @BUFI           ;CLEAR BUFFER
24  01374  020217  PR0B:   LDA 0,OFILE
25  01375  024241          LDA 1,LOBUF
26  01376  006277          DWRIT
27  01377  006273          DWAIT
28  01400  010217          ISZ OFILE
29  01401  014210          DSZ KNT
30  01402  000772          JMP PR0B
31
32  01403  020206  PR0C:   LDA 0,DISP
33  01404  024201          LDA 1,MOD
34  01405  152520          SUBZL 2,2           ;=1
35  01406  125015          MOV# 1,1,SNR        ;SKIP IF MOD=1,2=TK,TR
36  01407  152400          NEG 2,2             ;MOD=0 = KS
37  01410  143000          ADD 2,0
38  01411  040206          STA 0,DISP
39
40  01412  006247          JSR @FPROS          ;POST PROCESS THE FILE
41  01413  006250          JSR @FFIX.
42  01414  010225          ISZ PRFLD           ;GET NEXT OUTPUT FILE NUMBER
43  01415  014404          DSZ PROFN           ;MORE FILES?
44  01416  000716          JMP PR2             ;YES
45  01417  002401          JMP @PRR            ;DONE
46
47  01420  000000  PRR:    0
48  01421  000000  PROFN:  0
49  01422  000000  PRLNG:  0
50  01423  000000  PTK:    0
51  01424  000000  PRCNT:  0
52
53  01425  152400  PRX.:   SUB 2,2
54  01426  000402          JMP PR.+1
```

```
14712 .MAIN
01
02  21427 152000 PR2:   ADC 2,2
03  21430 250540        STA 2,PRMDE
04  21431 254536        STA 3,PRP
05  21432 240770        STA 0,PRLNG      ;# OF BLOCKS
06  21433 244770        STA 1,PTK        ;# OF POINTS/BLOCK (OUTPUT)
07  21434 244770        STA 1,PRCNT
08
09
10  21435 320137 PR1:   LDA 0,CNT        ;# OF INPUT FILES
11  21436 340210        STA 0,KNT
12  21437 102400        SUB 0,0
13  21440 340207        STA 0,FILE       ;INPUT FILE # DISPLACEMENT
14
15  21441 224207 PR0:   LDA 1,FILE
16  21442 230254        LDA 2,LITAB
17  21443 234255        LDA 3,LOTAB
18  21444 133000        ADD 1,2
19  21445 137000        ADD 1,3
20  21446 321000        LDA 0,0,2
21  21447 240202        STA 0,IPTR       ;INPUT INDEX WITHIN BLOCK
22  21450 321400        LDA 0,0,3
23  21451 240203        STA 0,OPTR       ;OUTPUT INDEX WITHIN BLOCK
24  21452 230242        LDA 2,LSTAB
25  21453 133000        ADD 1,2
26  21454 321002        LDA 0,0,2        ;INPUT FILE SCALE FACTOR
27  21455 230216        LDA 2,SCAL       ;SMALLEST SCALE FACTOR
28  21456 112400        SUB 0,2          ;AC2=# OF BITS TO SHIFT
29  21457 254512        STA 2,SHFTK
30
31  21460 230243        LDA 2,LDKTAB     ;ADR OF DKTAB
32  21461 133000        ADD 1,2
33  21462 321000        LDA 0,0,2        ;AC0 = ADR OF DESIRED INPUT SECTOR
34  21463 304562        JSR PRSG         ;GET IT IF NEEDED
35  21464 204576        JSR WPRS         ;MOVE FROM IBUF TO OBUF VIA POINTERS
36
37  21465 320202        LDA 0,IPTR       ;PREPARE TO UPDATE POINTERS
38  21466 224207        LDA 1,FILE
39  21467 230254        LDA 2,LITAB
40  21470 133000        ADD 1,2
41  21471 234243        LDA 3,LDKTAB
42  21472 137000        ADD 1,3
43  21473 224220        LDA 1,IDELT      ;INPUT DELTA FACTOR
44  21474 123000        ADD 1,0
45  21475 224264        LDA 1,MASKR      ;CORRECT THE POINTER ANYWAY
46  21476 107400        AND 0,1
47  21477 245000        STA 1,0,2        ;RETURN POINTER TO TABLE (ITAB)
48  21500 224266        LDA 1,K4
49  21501 231400        LDA 2,0,3        ;GET DISK ADR
50  21502 133000        ADD 1,2          ;+4 TO ADR
51  21503 224265        LDA 1,MASKL      ;OVERFLOW MASK
52  21504 107414        AND# 0,1,SZR
53  21505 251400        STA 2,0,3        ;HAVE OVERFLOW, UPDATE ADDRESS
```

```
10413 .MAIN
01
02  01506 020203           LDA 0,OPTR
03  01507 030255           LDA 2,LOTAB
04  01510 024207           LDA 1,FILE
05  01511 133000           ADD 1,2           ;TABLE ENTRY ADDRESS
06  01512 024221           LDA 1,ODELT       ;OUTPUT DELTA FACTOR
07  01513 123000           ADD 1,0
08  01514 034264           LDA 3,MASKR       ;MASK TO CORRECT POINTERS
09  01515 117400           AND 0,3
10  01516 055000           STA 3,0,2         ;SAVE POINTER FOR NEXT TIME
11  01517 030451           LDA 2,PRMDE       ;CHECK PROCESSING MODE
12  01520 151015           MOV# 2,2,SNR
13  01521 000422           JMP PR0D0         ;PROCESSING RESIDUAL BLOCK
14
15  01522 024265           LDA 1,MASKL       ;MASK TO DETECT OVERFLOW
16  01523 107415           AND# 0,1,SNR      ;NORMAL BLOCK PROCESS
17  01524 000715           JMP PR0           ;MORE IN BLOCK TO DO
18  01525 010207           ISZ FILE          ;USE NEXT INPUT FILE
19  01526 014676           DSZ PRCNT
20  01527 000712           JMP PR0           ; CONTINUE
21
22  01530 063610           SKPDN TTI         ;CHECK FOR ESCAPE CHAR TYPED
23  01531 000407           JMP PR0A          ;NO CHAR IN TTI
24  01532 060610           DIAC 0,TTI        ;HAVE A CHAR, GO CHECK IT
25  01533 024256           LDA 1,K177        ;MASK OFF PARITY BIT
26  01534 123400           AND 1,0
27  01535 024376           LDA 1,KESC        ;SYSTEM ABORT CHAR
28  01536 166435           SUBZ# 0,1,SNR
29  01537 002017           ABORT             ;=ESC, OR ALTMODE, ETC.
30  01540 020663 PR0A:     LDA 0,PTK
31  01541 040663           STA 0,PRCNT
32  01542 000410           JMP PR0D          ;OUTPUT BUFFER
33
34  01543 014661 PR0D0:    DSZ PRCNT         ;HERE ON PARTIAL BLOCK
35  01544 000675           JMP PR0           ;MORE POINTS TO DO
36  01545 020656           LDA 0,PTK
37  01546 040656           STA 0,PRCNT       ;RESET COUNTER
38  01547 010207           ISZ FILE          ;YES, GO TO NEXT INPUT FILE #
39  01550 014210           DSZ KNT           ;COUNT IT
40  01551 000670           JMP PR0           ;MORE TO DO
41
42  01552 020217 PR0D:     LDA 0,OFILE       ;NOW WRITE OUT THE BUFFER
43  01553 024266           LDA 1,K4
44  01554 107000           ADD 0,1
45  01555 044217           STA 1,OFILE       ;NEXT OFILE=OFILE+4
46  01556 024241           LDA 1,LOBUF
47  01557 034277           LDA 3,WRITE
48  01560 032266           LDA 2,K4
49  01561 005401           JSR 1,3           ;MULTIPLE WRITE
50  01562 006273           DWAIT
51  01563 006262           JSR @BUFI         ;CLEAR BUFFER
52
53  01564 014636           DSZ PRLNG         ;COUNT SECTORS/FILE (OUTPUT)
54  01565 000650           JMP PR1           ;NOT DONE WITH OUTPUT FILE
55  01566 002401           JMP @PRP
56
57  01567 000000 PRP:      0
58  01570 000000 PRMDE:    0
59  01571 000000 SHFTK:    0
```

```
1,414 ,MAIN
01
02                  ;ROUTINE TO CREATE ITAB OR OTAB TABLES
03
04  01572 054437 TFILL:  STA 3,TFR
05  01573 201400         LDA 0,0,3
06  01574 040436         STA 0,TFLOC    ;TABLE ADDRESS
07  01575 027401         LDA 1,1,3      ;DELTA BETWEEN FILE ENTRIES
08  01576 220137         LDA 0,CNT
09  01577 040434         STA 0,TFKNT    ;LOOP COUNTER
10  01600 230137         LDA 2,CNT      ;USE AS A LIMIT VALUE
11  01601 220206         LDA 0,DISP     ;INITIAL TABLE VALUE
12  01602 112033         ADCZ# 0,2,SNC  ;SKIP IF AC0 < AC2
13  01603 102400         SUB 0,0        ;RESET VALUE=0 FOR TABLE
14  01604 234201         LDA 3,MOD      ;CHECK FOR TK MODE (=1)
15  01605 175232         MOVZR# 3,3,SZC ;SKIP IF =0,2
16  01606 220206         LDA 0,DISP     ;USE DISP IF MOD=1=TK
17  01607 040425         STA 0,TFTMP    ;SAVE OUR VALUE
18  01610 234233 TF0:    LDA 3,DPF      ;0=SP, <>0=DP
19  01611 175004         MOV 3,3,SZR
20  01612 101120         MOVZL 0,0      ;CORRECT FOR DP
21  01613 042417         STA 0,@TFLOC   ;PUT INTO TABLE
22  01614 010416         ISZ TFLOC      ;POINT TO NEXT ENTRY
23  01615 020417         LDA 0,TFTMP
24  01616 123000         ADD 1,0        ;COMPUT NEXT ENTRY VALUE
25
26  01617 234201         LDA 3,MOD      ;CHECK MOD TYPE
27  01620 175232         MOVZR# 3,3,SZC ;SKIP IF MOD=0,2=KS,TR
28  01621 000403         JMP TF1        ;MOD=1=TK
29
30  01622 112033         ADCZ# 0,2,SNC  ;SKIP IF AC0 < AC2 (CHECK LIMITS)
31  01623 102400         SUB 0,0        ;RESET VALUE AC0 => AC2
32  01624 040410 TF1:    STA 0,TFTMP
33  01625 014406         DSZ TFKNT
34  01626 000762         JMP TF0
35  01627 234402         LDA 3,TFR      ;RETURN
36  01630 001402         JMP 2,3
37
38  01631 000000 TFR:    0
39  01632 000000 TFLOC:  0
40  01633 000000 TFKNT:  0
41  01634 000000 TFTMP:  0
42
43
44                  ;ROUTINE TO INITIALIZE (CLEAR) THE OUTPUT BUFFER
45
46  01635 024365 XBUF:   LDA 1,MASKL    ;=-1024.
47  01636 030241         LDA 2,LOBUF    ;ADR OF BUFFER
48  01637 102400         SUB 0,0
49  01640 041000 BUFI0:  STA 0,0,2
50  01641 151400         INC 2,2
51  01642 125404         INC 1,1,SZR
52  01643 000775         JMP BUFI0
53  01644 001400         JMP 0,3
```

```
1015 .MAIN
01
02                    ;AC0 = ADR OF DISK SECTOR WANTED FOR INPUT.
03                    ;IF NOT ALREADY IN IBUF, READ IT IN
04
05  01645 054413 PRSG:   STA 3,PRSGR
06  01646 024413        LDA 1,PRSGO      ;ALREADY IN CORE?
07  01647 106435        SUBZ# 0,1,SNR    ;SKIP IF BLOCK NOT IN CORE ALREADY
08  01650 002410        JMP @PRSGR       ;HERE IF AC0=>AC1 & AC0<AC3
09  01651 024240        LDA 1,LIBUF
10  01652 040407        STA 0,PRSGO      ;UPDATE OLD ADDRESS
11  01653 030266        LDA 2,K4
12  01654 034276        LDA 3,READ
13  01655 005401        JSR 1,3          ;DO MULTIPLE READ
14  01656 006273        DWAIT
15  01657 002401        JMP @PRSGR
16  01660 000000 PRSGR:  0
17  01661 177777 PRSGO:  -1
18
19                    ;MOVE A WORD FROM THE INPUT BUFFER 'IBUF' INDEX BY IPTR
20                    ;TO THE OUPUT BUFFER 'OBUF' INDEXED BY OPTR
21                    ;SHFTK=# OF RIGHT SHIFTS TO CORRECT DATA WITH
22
23  01662 054442 WPRS:   STA 3,WPRSR      ;SAVE RETURN ADR
24  01663 024233        LDA 1,DPF        ;CHECK FILE TYPE
25  01664 030240        LDA 2,LIBUF      ;ADR OF IBUF
26  01665 020202        LDA 0,IPTR       ;INDEX INTO IBUF
27  01666 113000        ADD 0,2          ;ADR OF ENTRY INTO BUFFER
28  01667 125004        MOV 1,1,SZR
29  01670 000406        JMP WPRS0        ;ENTRY IS DP
30  01671 025000        LDA 1,0,2        ;IS SP
31  01672 102400        SUB 0,0          ;FAKE A DP #
32  01673 125132        MOVZL# 1,1,SZC
33  01674 100000        COM 0,0
34  01675 000403        JMP WPRS4
35  01676 021000 WPRS0:  LDA 0,0,2       ;ENTRY IS DP
36  01677 025001        LDA 1,1,2
37  01700 030671 WPRS4:  LDA 2,SHFTK     ;# OF BITS TO SHIFT
38  01701 151005        MOV 2,2,SNR
39  01702 000407        JMP WPRS1        ;DON'T SHIFT
40  01703 101132 WPRS2:  MOVZL# 0,0,SZC  ;CHECK SIGN
41  01704 101241        MOVOR 0,0,SKP    ;IS -
42  01705 101220        MOVZR 0,0        ;IS +
43  01706 125200        MOVR 1,1
44  01707 151404        INC 2,2,SZR
45  01710 000773        JMP WPRS2
46  01711 030203 WPRS1:  LDA 2,OPTR      ;INDEX INTO OBUF
47  01712 034241        LDA 3,LOBUF     ;ADR OF OBUF
48  01713 157000        ADD 2,3          ;ADR OF OBUF ENTRY
49  01714 030233        LDA 2,DPF
50  01715 151004        MOV 2,2,SZR
51  01716 000403        JMP WPRS3       ;FILE IS DP
52  01717 045400        STA 1,0,3       ;SP
53  01720 002404        JMP @WPRSR      ;EXIT
54  01721 041400 WPRS3:  STA 0,0,3      ;DP
55  01722 045401        STA 1,1,3
56  01723 002401        JMP @WPRSR
57  01724 000000 WPRSR:  0
```

```
16  .MAIN
21
22              ;ROUTINE TO RETRIEVE A FINFO SECTOR AND
23              ;RETURN A POINTER IN AC2 TO THE ENTRY FOR A
24              ;FILE WHOSE FINFO SECTOR HAS BEEN READ INTO CORE.
25              ;INPUT FILE # IN AC0
26              ;OUTPUT ADR OF ENTRY IN CORE BUFFER IN AC2
27
28  21725 101132  .FGET:  MOVZL# 0,0,SZC
29  21726 001400          JMP 0,3         ;ILLEGAL FILE #
10  21727 103122          ADDZL 0,0,SZC   ;4X
11  21730 001400          JMP 0,3         ;ILLEGAL # - TOO BIG
12  21731 024252          LDA 1,K1774K    ;=177400
13  21732 107700          ANDS 0,1        ;DISP FOR FINFO START
14  21733 030251          LDA 2,K377      ;=377
15  21734 113400          AND 0,2         ;INDEX WITHIN SECTOR
16  21735 020145          LDA 0,FINCT     ;# OF FINFO SECTORS
17  21736 106432          SUBZ# 0,1,SZC   ;SKIP IF AC0 > AC1
18  21737 001400          JMP 0,3         ;ILLEGAL - FILE # TOO BIG FOR FINFO
19  21740 020172          LDA 0,PFINFO    ;ADR OF FINFO SECTOR
20  21741 123000          ADD 1,0         ;ADR OF REQUIRED SECTOR
21  21742 024416          LDA 1,FGOLD     ;IS IT IN CORE ALREADY?
22  21743 106435          SUBZ# 0,1,SNR
23  21744 000411          JMP FGET0       ;YES, ALREADY IN CORE
24  21745 054415          STA 3,FGES3     ;NO, PREPARE TO READ IT
25  21746 050413          STA 2,FGES2     ;SAVE AC2,AC3
26  21747 040411          STA 0,FGOLD     ;UPDATE FGOLD
27  21750 024244          LDA 1,LFBUF     ;ADR FOR FINFO CORE BUFFER
28  21751 006276          DREAD
29  21752 006273          DWAIT
30  21753 030406          LDA 2,FGES2     ;RESTORE (INDEX INT BUFFER)
31  21754 034406          LDA 3,FGES3     ;RETURN ADR
32  21755 020244  FGET0:  LDA 0,LFBUF     ;ADR OF BUFFER IN CORE
33  21756 113000          ADD 0,2         ;ADR OF ENTRY IN CORE = AC2
34  21757 001401          JMP 1,3         ;GOOD RETURN
35  21760 177777  FGOLD:  -1
36  21761 200000  FGES2:  0
37  21762 200000  FGES3:  0
38
39              ;UPDATE FINFO FOR FILE WHOSE NUMBER IS IN "PRFLD"
40
41  21763 054423  FUP:    STA 3,FUPR
42  21764 020226          LDA 2,PRFLD
43  21765 006245          JSR @FGET
44  21766 002420          JMP @FUPR
45  21767 020237          LDA 0,SECL      ;# OF SECTORS IN OUTPUT FILE
46  21770 024233          LDA 1,DPF       ;DR FLAG
47  21771 123000          ADD 1,0
48  21772 041000          STA 0,0,2
49  21773 020212          LDA 0,NSCN
50  21774 041001          STA 0,1,2
51  21775 020216          LDA 0,SCAL
52  21776 041002          STA 0,2,2
53  21777 020215          LDA 0,PEAK
54  22000 041003          STA 0,3,2
55  22001 020757          LDA 0,FGOLD
56  22002 024244          LDA 1,LFBUF
57  22003 006277          DWRIT
58  22004 006273          DWAIT
59  22005 002401          JMP @FUPR
60  22006 200000  FUPR:   0
```

```
0217 .MAIN
01
02                 ;ROUTINES FPR AND FFX
03                 ;FPR
04                 ;INPUT FILE # IN "PRELD"
05                 ;OUTPUT AC0,1 = AVERAGE BACKGROUND VALUE
06                 ;OUTPUT "PEAK" = LOCATION OF PEAK VALUE
07                 ;CALL+1 = NORMAL RETURN
08                 ;
09                 ;FFX
10                 ;INPUT FILE # IN "PRELD"
11                 ;INPUT AC0,1 = AVERAGE BACKGROUND VALUE
12                 ;OUTPUT:
13                 ;READS THE FILE AND SUBTRACTS THE AVERAGE BACKGOUND
14                 ;VALUE FROM EACH POINT IN THE FILE AND RE-WRITES THE
15                 ;FILE BACK OUT. WHEN DONE, THE FINFO ENTRY FOR THE
16                 ;FILE IS UPDATED USING "GEW","NSCN","SCAL", AND
17                 ;"PEAK"
18
19  02207 354466 FFX:  STA 3,FPRR
20  02210 240467       STA 0,FPSUM       ;SAVE AVERAGE BACKGROUND VALUE IN
21  02211 244467       STA 1,FPSUM+1     ;"FPSUM"
22  02212 107020       ADDZ 0,1          ;TEST FOR ZERO AVERAGE BG VALUE
23  02213 125605       INCR 1,1,SNR      ;SKIP IF AC0 OR AC1 <> 0
24  02214 000414       JMP FFX0          ;AV BG VAL=0
25  02215 020227       LDA 0,SOFILE      ;ADR OF STARTTT OF CURRENT OUTPUT FILE
26  02216 040465       STA 0,FADR
27  02217 020222       LDA 0,ONSEC       ;# OF WHOLE OUTPUT BLOCKS
28  02220 024235       LDA 1,PTZ         ;# OF POINTS/SECTOR
29
30  02221 004571       JSR FPBS          ;DO AV BG SUB
31
32  02222 020137       LDA 0,CNT         ;COMPUT # OF RESIDUAL POINTS
33  02223 024234       LDA 1,RES
34  02224 006257       JSR PMULT         ;# POINTS = RES * CNT
35  02225 102520       SUBZL 0,0         ;# OF BLOCKS=1
36  02226 125004       MOV 1,1,SZR       ;CHECK FOR 0 RESIDUAL POINTS
37  02227 004563       JSR FPBS          ;HAVE SOME - GO PROCESS
38
39  02230 006454 FFX0: JSR @LFUP         ;UPDATE FINFO
40  02231 002444       JMP @FPRR         ;EXIT
```

```
FPMR .MAIN
01
02  02032 354143  FPR:    STA  3,FPRR
03  02033 176400          SUB  3,3
04  02034 354442          STA  3,FPLOC    ;PEAK LOCATION INDICATOR
05  02035 354442          STA  3,FPSUM    ;DP SUM REGISTER
06  02036 254442          STA  3,FPSUM+1
07  02037 254215          STA  3,PEAK
08  02040 254441          STA  3,PKVAL    ;INIT DP PEAK VALUE
09  02041 354441          STA  3,PKVAL+1
10
11  02042 220227          LDA  0,SOFILE   ;ADR OF OUR OUTPUT FILE
12  02043 240443          STA  0,FADR
13  02044 320222          LDA  0,ONSEC    ;# OF WHOLE OUTPUT BLOCKS
14  02045 324235          LDA  1,PTZ      ;# OF POINTS/SECTOR
15
16  02046 304444          JSR  FPAP       ;COMPUT AV BG VAL, FIND PEAK
17
18  02047 320137          LDA  0,CNT      ;COMPUTE # OF RESIDUAL POINTS
19  02050 224234          LDA  1,RES
20  02051 206257          JSR  @MULT
21  02052 102520          SUBZL 0,0       ;# OF SECTORS = 1
22  02053 125004          MOV  1,1,SZR    ;SKIP IF NO RESIDUAL POINTS
23  02054 304436          JSR  FPAP       ;PROCESS RESIDUALS
24
25  02055 220204          LDA  0,PNTS
26  02056 224205          LDA  1,PNTS+1   ;DP. # OF POINTS
27  02057 240410          STA  0,FPRQ     ;PREPARE TO COMPUTE AV BG VAL
28  02060 244410          STA  1,FPRQ+1
29
30  02061 220416          LDA  0,FPSUM    ;RUNNING SUM
31  02062 224416          LDA  1,FPSUM+1
32  02063 240422          STA  0,FPSGN    ;SAVE SIGN OF DP NUMBER
33  02064 101132          MOVZL# 0,0,SZC  ;TEST AND TAKE ABS VAL
34  02065 304421          JSR  DNEG       ;IS - TAKE ABS VAL
35  02066 206246          JSR  @DIVIDE
36  02067 200000  FPRQ:   0
37  02070 200000          0
38  02071 234414          LDA  3,FPSGN    ;TEST SIGN FOR RESULT
39  02072 175132          MOVZL# 3,3,SZC
40  02073 304413          JSR  DNEG       ;CORRECT SIGN
41  02074 002401          JMP  @FPRR      ;AC0,1 = AV BG VAL
42
43  02075 200000  FPRR:   0
44  02076 200000  FPLOC:  0
45  02077 200002  FPSUM:  .BLK 2
46  02101 200002  PKVAL:  .BLK 2
47  02103 200000  FADR:   0
48  02104 301763  LFUP:   EUP
49  02105 200000  FPSGN:  0
50
51  02106 124405  DNEG:   NEG  1,1,SNR    ;DP NEGATE (AC0,1)
52  02107 100401          NEG  0,0,SKP
53  02110 100000          COM  0,0
54  02111 001400          JMP  0,3
```

```
10019 .MAIN
01
02              ;ROUTINE TO DO PEAK LOCATION AND AVERAGE VALUE SUMMATION
03              ;INPUT:
04              ;AC0=#OF BLOCKS
05              ;AC1=# OF POINTS/BLOCK
06              ;PEAK LEFT IN "FPLOC" & "PEAK"
07              ;SUM LEFT IN "FPSUM, FPSUM+1"
08
09 02112 354473 FPAP:   STA 3,FPAPR
10 02113 244475         STA 1,FPACT     ;# OF POINTS/BLOCK
11 02114 244473         STA 1,FPAPK
12 02115 240471         STA 0,FPAPS     ;# OF BLOCKS
13
14 02116 220765 FPAP2:  LDA 0,FADR      ;SECTOR ADR
15 02117 224266         LDA 1,K4
16 02120 107000         ADD 0,1
17 02121 244762         STA 1,FADR      ;FADR=FADR+4
18 02122 224240         LDA 1,LIBUF
19 02123 244466         STA 1,FPAPI     ;USE AS A POINTER
20 02124 230266         LDA 2,K4
21 02125 234276         LDA 3,READ
22 02126 006401         JSR 1,3         ;MULTIPLE READ
23 02127 006273         DWAIT
24
25 02130 330461 FPAP4:  LDA 2,FPAPI     ;POINT INTO BUFFER
26 02131 234233         LDA 3,DPF       ;DP FLAG
27 02132 175004         MOV 3,3,SZR
28 02133 000406         JMP FPAP0       ;IS DP
29 02134 102400         SUB 0,0         ;IS SP FAKE DP
30 02135 225000         LDA 1,0,2
31 02136 125132         MOVZL# 1,1,SZC
32 02137 100000         COM 0,0
33 02140 000404         JMP FPAP1
34 02141 021000 FPAP0:  LDA 0,0,2
35 02142 025001         LDA 1,1,2
36 02143 010446         ISZ FPAPI
37 02144 010445 FPAP1:  ISZ FPAPI
```

```
 1 02202 .MAIN
 2 ;
 3 02145 232732        LDA 2,FPSUM
 4 02146 234732        LDA 3,FPSUM+1
 5 02147 137222        ADDZ 1,3,SZC    ;C(2,3)=C(2,3)+C(0,1)
 6 02150 151400        INC 2,2
 7 02151 113000        ADD 0,2
 8 02152 252725        STA 2,FPSUM
 9 02153 254725        STA 3,FPSUM+1
10 ;
11 02154 101133        MOVZL# 0,0,SNC  ;TAKE ABS VALUE
12 02155 000404        JMP .+4
13 02156 124405        NEG 1,1,SNR
14 02157 100401        NEG 0,0,SKP
15 02160 100000        COM 0,0
16 ;
17 02161 230720        LDA 2,PKVAL     ;PREVIOUS VALUE OF PEAK
18 02162 234720        LDA 3,PKVAL+1
19 02163 136422        SUBZ 1,3,SZC    ;C(2,3)=C(2,3)-C(0,1)
20 02164 112401        SUB 0,2,SKP
21 02165 112000        ADC 0,2
22 ;
23 02166 151133        MOVZL# 2,2,SNC  ;CHECK SIGN OF RESULT
24 02167 000405        JMP FPAP3       ;=+ NO NEW PEAK
25 02170 240711        STA 0,PKVAL     ;HAVE A NEW PEAK, SAVE THE VALUE
26 02171 244711        STA 1,PKVAL+1
27 ;
28 02172 324704        LDA 2,FPLOC
29 02173 240715        STA 0,PEAK
30 ;
31 02174 010702 FPAP3: ISZ FPLOC
32 02175 000401        401
33 02176 014412        DSZ FPACT
34 02177 000731        JMP FPAP4
35 ;
36 02200 220407        LDA 0,FPAPK
37 02201 240407        STA 0,FPACT     ;RESET COUNTER
38 02202 014404        DSZ FPAPS       ;COUNT BLOCKS
39 02203 000713        JMP FPAP2       ;DO ANOTHER BLOCK
40 02204 002401        JMP @FPAPR      ;EXIT
41 ;
42 02205 000000 FPAPR: 0
43 02206 000000 FPAPS: 0
44 02207 000000 FPAPK: 0
45 02210 000000 FPACT: 0
46 02211 000000 FPAPI: 0
```

```
1,2021 .MAIN.
01                  ;ROUTINE TO DO AVERAGE BACKGROUND SUBTRACT
02                  ;INPUT:
03                  ;AC0=# OF BLOCKS
04                  ;AC1=# OF POINTS/BLOCK
05                  ;AVERAGE BG VAL IN "FPSUM"
06
07  02212 054773 FPBS:  STA 3,FPAPR
08  02213 014774        STA 1,FPAPK
09  02214 044774        STA 1,FPACT
10  02215 040771        STA 0,FPAPS     ;# OF BLOCKS
11
12  02216 020665 FPBS0: LDA 0,FADR
13  02217 024241        LDA 1,LOBUF     ;BUFFER ADR
14  02220 044771        STA 1,FPAPI     ;POINTER
15  02221 030266        LDA 2,K4
16  02222 034276        LDA 3,READ
17  02223 005401        JSR 1,3         ;MULTIPLE READ
18  02224 006273        DWAIT
19
20  02225 030764 FPBS1: LDA 2,FPAPI
21  02226 024233        LDA 1,DPF
22  02227 125004        MOV 1,1,SZR
23  02230 000406        JMP FPBS2       ;IS DP.
24  02231 102400        SUB 0,0         ;IS SP, FAKE DP
25  02232 025000        LDA 1,0,2
26  02233 125132        MOVZL# 1,1,SZC
27  02234 100000        COM 0,0
28  02235 000403        JMP FPBS3
29  02236 021000 FPBS2: LDA 0,0,2
30  02237 025001        LDA 1,1,2
```

```
      .AIN
01
02  02240 030637 FPBS3:  LDA 2,FPSUM
03  02241 034637         LDA 3,FPSUM+1    ;GET AV VAL
04  02242 166122         SUBZ 3,1,SZC     ;C(0,1)=C(0,1)-C(2,3)
05  02243 142401         SUB 2,0,SKP
06  02244 142000         ADC 2,0
07
08  02245 030744         LDA 2,FPAPI
09  02246 034233         LDA 3,DPF
10  02247 175004         MOV 3,3,SZR
11  02250 000403         JMP FPBS4        ;IS DP
12  02251 045000         STA 1,0,2        ;IS SP
13  02252 000404         JMP FPBS5
14  02253 041000 FPBS4:  STA 0,0,2
15  02254 045001         STA 1,1,2
16  02255 010734         ISZ FPAPI
17  02256 010733 FPBS5:  ISZ FPAPT
18
19  02257 014731         DSZ FPACT        ;COUNT A POIN PROCESSED
20  02260 000745         JMP FPBS1
21
22  02261 020602         LDA 0,FADR       ;REWRITE THE BUFFER
23  02262 024066         LDA 1,K4
24  02263 137000         ADD 0,1
25  02264 044617         STA 1,FADR
26  02265 024241         LDA 1,LOBUF
27  02266 030066         LDA 2,K4
28  02267 034077         LDA 3,WRITE
29  02270 005401         JSR 1,3
30  02271 006273         DWAIT
31
32  02272 020715         LDA 0,FPAPK      ;REINIT COUNTER
33  02273 040715         STA 0,FPACT
34  02274 014712         DSZ FPAPS        ;COUNT A BLOCK PROCESSED
35  02275 000721         JMP FPBS0        ;DO ANOTHER ONE
36  02276 002707         JMP @FPAPR       ;DONE
```

```
12323 .MAIN
01
02                      ;ROUTINE TO DIVIDE THE DP # IN AC0,1 BY THE DP
03                      ;# AT CALL+1,+2.  A DP QUOTIENT RESULTS, THERE
04                      ;REMAINDER IN AC2,AC3.  ALL NUMBERS ARE POSITIVE
05                      ;OUTPUT DP QUOTIENT IN AC0,AC1
06
07  02277 354453  DIVX: STA 3,DIVR         ;SAVE AC3
08  02300 240453        STA 0,DIVDD        ;SAVE DIVIDEND
09  02301 244453        STA 1,DIVDD+1
10  02302 031400        LDA 2,0,3          ;GET DIVISOR MSH
11  02303 035401        LDA 3,1,3          ;DIVISOR LSH
12  02304 020456        LDA 0,DIV32        ;1=32
13  02305 040454        STA 0,DIVK         ;LOOP COUNTER
14  02306 102400        SUB 0,0
15  02307 040446        STA 0,DIVWR        ;INIT WORKING REGISTER
16  02310 040446        STA 0,DIVWR+1
17
18  02311 020442  DIV2: LDA 0,DIVDD        ;GET DIVIDEND
19  02312 024442        LDA 1,DIVDD+1
20  02313 125100        MOVL 1,1
21  02314 101100        MOVL 0,0           ;CARRY = MSH OF DIVIDEND
22  02315 040436        STA 0,DIVDD        ;SAVE DIVIDEND
23  02316 044436        STA 1,DIVDD+1
24  02317 020436        LDA 0,DIVWR        ;GET WORKING REGISTER
25  02320 024436        LDA 1,DIVWR+1
26  02321 125100        MOVL 1,1           ;MOVE INTO WORKING REGISTER
27  02322 101100        MOVL 0,0
28  02323 040432        STA 0,DIVWR        ;SAVE WORKING REGISTER
29  02324 044432        STA 1,DIVWR+1
30  02325 166422        SUBZ 3,1,SZC       ;DP SUBTRACT (WR - DIVISOR)
31  02326 142401        SUB 2,0,SKP
32  02327 142000        ADC 2,0            ;IF RESULT IS NEG, SHIFT IN 0
33  02330 101132        MOVZL# 0,0,SZC     ;ELSE SHIFT 1 INTO RESULT
34  02331 000403        JMP DIV1           ;WORKING REG < DIVISOR
35  02332 040423        STA 0,DIVWR        ;WR => DIVISOR, UPDATE WR
36  02333 044423        STA 1,DIVWR+1
37
38  02334 101100  DIV1: MOVL 0,0           ;SET THE CARRY BIT = SIGN BIT
39  02335 020422        LDA 0,DIVQ         ;GET QUOTIENT
40  02336 024422        LDA 1,DIVQ+1
41  02337 125160        MOVCL 1,1          ;SHIFT COMPLEMENT OF CARRY INTO IT
42  02340 101100        MOVL 0,0
43  02341 040416        STA 0,DIVQ         ;SAVE QUOTIENT
44  02342 044416        STA 1,DIVQ+1
45  02343 014416        DSZ DIVK           ;COUNT A PASS THROUGH LOOP
46  02344 000745        JMP DIV2
47
48  02345 010405        ISZ DIVR           ;COMPUTE RETURN ADR
49  02346 010404        ISZ DIVR
50  02347 030406        LDA 2,DIVWR        ;REMAINDER
51  02350 034406        LDA 3,DIVWR+1
52  02351 002401        JMP @DIVR          ;EXIT
53
54  02352 000000  DIVR: 0
55  02353 000002  DIVDD: .BLK 2
56  02355 000002  DIVWR: .BLK 2
57  02357 000002  DIVQ:  .BLK 2
58  02361 000000  DIVK:  0
59  02362 000040  DIV32: 32.
```

```
01  ;24  .MAIN
02
03        200001 .TXTM 1
04
05  02363 306412 CRETX: .TXT "<15><12>?"
06         237440
07         200000
08  02366 243114 FLSTX: .TXT "FLS ERROR"
09         251440
10         242522
11         251117
12         251000
13  02373 241516 CNTTX: .TXT "CNT ERROR"
14         252240
15         242522
16         251117
17         251000
18  02400 343114 FLDTX: .TXT "FLD ERROR"
19         242040
20         242522
21         251117
22         251000
23  02405 343114 FLOTX: .TXT "FLS,FLD OVERLAP"
24         351454
25         343114
26         242040
27         247526
28         242522
29         246101
30         250000
31  02415 343114 FINTX: .TXT "FLS,FLD <76> FINFO"
32         251454
33         343114
34         242040
35         337040
36         243111
37         247106
38         247400
39  02425 343114 FSTTX: .TXT "FLS1S DIFFER <55> SIZE,TYPE"
40         251447
41         251440
42         242111
43         243106
44         242522
45         223055
46         320123
47         344532
48         242454
49         252131
50         250105
51         000000
52  02442 343114 FSTBTX: .TXT "FLS<76>DISK END"
53         251476
54         342111
55         351513
56         320105
57         247104
58         000000
59  02451 343114 FDTBTX: .TXT "FLD<76>DISK END"
60         242076
61         242111
```

```
0025 .MAIN
01      251513
02      220125
03      247104
04      200300
05 02460 343111 FETX:   .TXT "FINFO ENTRY ERROR"
06      247106
07      247140
08      242516
09      252122
10      254440
11      242522
12      251117
13      251000
14 02471 241516 CNFSX:  .TXT "CNT*(FLS,FLD) LENGTH <76> 32767."
15      252052
16      224106
17      246123
18      226106
19      246104
20      224440
21      246105
22      247107
23      252110
24      220076
25      220063
26      231067
27      233067
28      227000
```

```
1P026 .MAIN
01
02 02510 304602 NEXTP:  IBUF
03 02511 202600         OBUF
04 02512 212600         STAB
05 02513 214600         DKTAB
06 02514 216600         EBUF
07 02515 201725         .FGET
08 02516 202277         DIVX
09 02517 202032         FPR
10 02520 202007         FEX
11 02521 000377         377
12 02522 177400         177400
13 02523 240000         40000
14 02524 206600         ITAB
15 02525 210600         OTAB
16 02526 200177         177
17 02527 201264         MULX
18 02530 201244         ICHKX
19 02531 000400         400
20 02532 201635         XBUFI
21 02533 201572         TFILL
22 02534 001777         001777
23 02535 176000         176000
24 02536 000004         4
25              FOO:
26              .END

**00000 TOTAL ERRORS, 00000 PASS 1 ERRORS
```

0027 .MAIN

| | | | | | | | |
|---|---|---|---|---|---|---|---|
| AFONT 002217 | 1/16 | 8/29 | 13/29 | | | | |
| ACAL 001121 | 7/02 | 7/11 | 7/35 | | | | |
| ACAL0 001131 | 7/39 | 7/43 | | | | | |
| ACAL1 001126 | 7/40 | 7/42 | | | | | |
| AMOD 000116 | 1/32 | 4/10 | | | | | |
| ATE1 000647 | 3/47 | 4/30 | | | | | |
| ATE11 000653 | 3/51 | 4/37 | 4/52 | 4/56 | | | |
| ATE2 000650 | 3/48 | 4/15 | | | | | |
| ATE6 000651 | 3/49 | 5/04 | | | | | |
| ATE7 000652 | 3/50 | 5/08 | | | | | |
| BUFL 000262 | 2/24 | 11/07 | 11/23 | 13/51 | | | |
| BUFIO 001640 | 14/49 | 14/52 | | | | | |
| CNFSX 002471 | 8/21 | 25/14 | | | | | |
| CNT 000137 | 1/27 | 4/13 | 5/29 | 6/27 | 6/32 | 9/01 | 10/08 |
| | 10/23 | 10/44 | 11/10 | 12/10 | 14/08 | 14/12 | 17/32 |
| | 18/18 | | | | | | |
| CNTTX 002373 | 8/25 | 24/12 | | | | | |
| CPFTX 002363 | 8/26 | 24/04 | | | | | |
| DISP 000206 | 1/39 | 10/24 | 11/32 | 11/38 | 14/11 | 14/16 | |
| DIV1 002334 | 23/34 | 23/38 | | | | | |
| DIV2 002311 | 23/18 | 23/46 | | | | | |
| DIV32 002362 | 23/12 | 23/59 | | | | | |
| DIVDD 002353 | 23/08 | 23/09 | 23/18 | 23/19 | 23/22 | 23/23 | 23/55 |
| DIVID 000246 | 2/12 | 5/44 | 5/48 | 6/06 | 18/35 | | |
| DIVK 002361 | 23/13 | 23/45 | 23/58 | | | | |
| DIVQ 002357 | 23/39 | 23/40 | 23/43 | 23/44 | 23/57 | | |
| DIVR 002350 | 23/07 | 23/48 | 23/49 | 23/52 | 23/54 | | |
| DIVWR 002355 | 23/15 | 23/16 | 23/24 | 23/25 | 23/28 | 23/29 | 23/35 |
| | 23/36 | 23/50 | 23/51 | 23/56 | | | |
| DIVX 002277 | 23/07 | 26/08 | | | | | |
| DKTAB 014600 | 1/12 | 1/13 | 26/05 | | | | |
| DMAX 000166 | 1/30 | 7/45 | | | | | |
| DMFG 002106 | 18/34 | 18/40 | 18/51 | | | | |
| DPF 000233 | 1/60 | 4/45 | 5/35 | 10/09 | 14/18 | 15/24 | 15/49 |
| | 16/46 | 19/26 | 21/21 | 22/09 | | | |
| DREAD 006276 | 1/19 | 3/13 | 4/07 | 16/28 | | | |
| DWAIT 006273 | 1/21 | 3/14 | 4/08 | 11/27 | 13/50 | 15/14 | 16/29 |
| | 16/58 | 19/23 | 21/18 | 22/30 | | | |
| DWRIT 006277 | 1/20 | 11/26 | 16/57 | | | | |
| EPR 001167 | 8/02 | 8/04 | 8/06 | 8/08 | 8/10 | 8/12 | 8/14 |
| | 8/16 | 8/18 | 8/20 | 8/23 | | | |
| EPRL 001174 | 8/24 | 8/28 | | | | | |
| EXEC 000150 | 1/15 | 9/16 | | | | | |
| FADR 002103 | 17/26 | 18/12 | 18/47 | 19/14 | 19/17 | 21/12 | 22/22 |
| | 22/25 | | | | | | |
| FBUF 016600 | 1/13 | 26/06 | | | | | |
| FDIST 002451 | 8/17 | 24/58 | | | | | |
| FETX 002460 | 8/19 | 25/05 | | | | | |
| FFIX 000250 | 2/14 | 11/41 | | | | | |
| FFX 002307 | 17/19 | 26/10 | | | | | |
| FFXU 002332 | 17/24 | 17/39 | | | | | |
| FGES2 001761 | 16/25 | 16/30 | 16/36 | | | | |
| FGES3 001762 | 16/24 | 16/31 | 16/37 | | | | |
| FGET 000245 | 2/11 | 4/29 | 5/03 | 5/22 | 16/43 | | |
| FGETD 001755 | 16/23 | 16/32 | | | | | |
| FGOLD 001760 | 16/21 | 16/26 | 16/35 | 16/55 | | | |
| FILE 000207 | 1/40 | 4/28 | 5/02 | 5/12 | 5/19 | 5/21 | 5/24 |
| | 12/13 | 12/15 | 12/38 | 13/04 | 13/18 | 13/38 | |
| FINCT 000145 | 1/28 | 16/16 | | | | | |

| | | | | | | | | |
|---|---|---|---|---|---|---|---|---|
| FINTX | 002415 | 8/11 | 24/33 | | | | | |
| FLC | 000365 | 1/25 | 5/18 | 7/12 | 10/06 | | | |
| FLDTX | 002400 | 8/07 | 24/17 | | | | | |
| FLOTX | 002405 | 8/09 | 24/22 | | | | | |
| FLS | 000112 | 1/26 | 4/27 | 7/03 | | | | |
| FLSTX | 002366 | 8/03 | 24/07 | | | | | |
| FND | 001120 | 7/09 | 7/20 | 7/33 | | | | |
| FOO | 002537 | 3/41 | 26/25 | | | | | |
| FPACT | 002210 | 19/10 | 20/32 | 20/36 | 20/44 | 21/09 | 22/19 | 22/33 |
| FPAP | 002112 | 18/16 | 18/23 | 19/09 | | | | |
| FPAP0 | 002141 | 19/28 | 19/34 | | | | | |
| FPAP1 | 002144 | 19/33 | 19/37 | | | | | |
| FPAP2 | 002116 | 19/14 | 20/38 | | | | | |
| FPAP3 | 002174 | 20/23 | 20/30 | | | | | |
| FPAP4 | 002130 | 19/35 | 20/33 | | | | | |
| FPAPI | 002211 | 19/19 | 19/25 | 19/36 | 19/37 | 20/45 | 21/14 | 21/20 |
| | | 22/08 | 22/16 | 22/17 | | | | |
| FPAPK | 002207 | 19/11 | 20/35 | 20/43 | 21/08 | 22/32 | | |
| FPAPR | 002205 | 19/09 | 20/39 | 20/41 | 21/07 | 22/36 | | |
| FPAPS | 002206 | 19/12 | 20/37 | 20/42 | 21/10 | 22/34 | | |
| FPBS | 002212 | 17/30 | 17/37 | 21/07 | | | | |
| FPBS0 | 002216 | 21/12 | 22/35 | | | | | |
| FPBS1 | 002225 | 21/20 | 22/28 | | | | | |
| FPBS2 | 002236 | 21/23 | 21/29 | | | | | |
| FPBS3 | 002240 | 21/28 | 22/02 | | | | | |
| FPBS4 | 002253 | 22/11 | 22/14 | | | | | |
| FPBS5 | 002256 | 22/13 | 22/17 | | | | | |
| FPLOC | 002276 | 18/04 | 18/44 | 20/27 | 20/30 | | | |
| FPR | 002332 | 18/02 | 26/09 | | | | | |
| FPRW | 002267 | 18/27 | 18/28 | 18/36 | | | | |
| FPROS | 000217 | 2/13 | 11/42 | | | | | |
| FPER | 002275 | 17/19 | 17/40 | 18/02 | 18/41 | 18/43 | | |
| FPSGN | 002105 | 18/32 | 18/38 | 18/49 | | | | |
| FPSUM | 002377 | 17/20 | 17/21 | 18/05 | 18/06 | 18/30 | 18/31 | 18/45 |
| | | 20/02 | 20/03 | 20/07 | 20/08 | 22/02 | 22/03 | |
| FST | 000230 | 1/57 | 7/08 | 7/19 | 10/46 | | | |
| FSTRT | 002443 | 8/15 | 24/51 | | | | | |
| FSTTX | 002425 | 8/13 | 24/38 | | | | | |
| FUP | 001763 | 16/41 | 18/48 | | | | | |
| FUPR | 002206 | 16/41 | 16/44 | 16/59 | 16/60 | | | |
| GEN | 000211 | 1/42 | 4/32 | 5/06 | | | | |
| IBUF | 004600 | 1/08 | 1/09 | 26/02 | | | | |
| ICHK | 000264 | 2/22 | 4/51 | 6/17 | | | | |
| ICHK0 | 001251 | 9/28 | 9/30 | | | | | |
| ICHKR | 001263 | 9/23 | 9/27 | 9/34 | 9/37 | 9/38 | | |
| ICHKX | 001244 | 9/23 | 26/18 | | | | | |
| IDELT | 000220 | 1/49 | 10/18 | 12/43 | | | | |
| IDSP | 000204 | 1/53 | 10/30 | 10/38 | | | | |
| IDTB | 000202 | 1/36 | 12/21 | 12/37 | 15/26 | | | |
| ITAB | 006600 | 1/09 | 1/10 | 10/37 | 26/14 | | | |
| K177 | 000256 | 2/20 | 13/25 | | | | | |
| K1774 | 000252 | 2/16 | 16/12 | | | | | |
| K377 | 000251 | 2/15 | 8/36 | 16/14 | | | | |
| K3777 | 000646 | 3/45 | 4/35 | | | | | |
| K4 | 000266 | 2/28 | 12/43 | 13/43 | 13/48 | 15/11 | 19/15 | 19/20 |
| | | 21/15 | 22/23 | 22/27 | | | | |
| K400 | 000261 | 2/23 | 4/42 | 5/34 | | | | |
| K40K | 000253 | 2/17 | 4/41 | | | | | |

GU29 .MAIN

| | | | | | | | | |
|---|---|---|---|---|---|---|---|---|
| KESC | 000376 | 1/23 | 13/27 | | | | | |
| KNT | 000210 | 1/41 | 4/16 | 5/13 | 5/17 | 5/25 | 9/02 | 9/11 |
| | | 10/45 | 11/05 | 11/22 | 11/29 | 12/11 | 13/39 | |
| KPGM | 000176 | 1/29 | 7/43 | | | | | |
| LOKTA | 000243 | 2/09 | 10/48 | 12/31 | 12/41 | | | |
| LFBUF | 000244 | 2/10 | 16/27 | 16/32 | 16/56 | | | |
| LFUP | 002104 | 17/39 | 18/48 | | | | | |
| LIBUF | 000240 | 2/06 | 2/07 | 2/08 | 2/09 | 2/10 | 2/11 | 2/12 |
| | | 2/13 | 2/14 | 2/15 | 2/16 | 2/17 | 2/18 | 2/19 |
| | | 2/20 | 2/21 | 2/22 | 2/23 | 2/24 | 2/25 | 2/26 |
| | | 2/27 | 2/28 | 3/40 | 4/06 | 4/09 | 15/09 | 15/25 |
| | | 19/18 | | | | | | |
| LITAB | 000254 | 2/18 | 12/16 | 12/39 | | | | |
| LOBUF | 000241 | 2/07 | 11/25 | 13/46 | 14/47 | 15/47 | 21/13 | 22/26 |
| LOTAB | 000255 | 2/19 | 12/17 | 13/03 | | | | |
| LSTAB | 000242 | 2/08 | 4/58 | 9/03 | 12/24 | | | |
| MASKL | 000265 | 2/27 | 12/51 | 13/15 | 14/46 | | | |
| MASKR | 000264 | 2/26 | 12/45 | 13/08 | | | | |
| MOD | 000201 | 1/35 | 4/11 | 10/21 | 11/33 | 14/14 | 14/26 | |
| MULT | 000257 | 2/21 | 5/30 | 6/22 | 6/34 | 6/39 | 17/34 | 18/20 |
| MULX | 001264 | 9/44 | 26/17 | | | | | |
| MULX0 | 001273 | 9/51 | 9/54 | | | | | |
| MULX1 | 001277 | 9/50 | 9/55 | | | | | |
| MULX2 | 001304 | 9/45 | 9/57 | 9/60 | | | | |
| MULXR | 001303 | 9/44 | 9/58 | 9/59 | | | | |
| NEXTA | 000630 | 3/05 | 3/30 | | | | | |
| NEXTB | 000635 | 3/07 | 3/35 | | | | | |
| NEXTC | 000641 | 3/19 | 3/39 | | | | | |
| NEXTD | 000642 | 3/20 | 3/40 | | | | | |
| NEXTE | 000643 | 3/21 | 3/41 | | | | | |
| NEXTP | 002510 | 3/39 | 3/41 | 26/02 | | | | |
| NSCN | 000212 | 1/43 | 4/34 | 16/49 | | | | |
| NSEC | 000213 | 1/44 | 4/38 | 4/50 | 4/53 | 5/28 | 7/04 | 10/47 |
| NXTC | 000644 | 3/06 | 3/09 | 3/15 | 3/42 | | | |
| NXTS | 000645 | 3/08 | 3/12 | 3/16 | 3/43 | | | |
| OBUF | 002600 | 1/07 | 1/08 | 26/03 | | | | |
| ODELT | 000221 | 1/50 | 10/12 | 13/06 | | | | |
| ODSP | 000225 | 1/54 | 10/27 | 10/42 | | | | |
| OFILE | 000217 | 1/48 | 7/17 | 10/33 | 11/24 | 11/28 | 13/42 | 13/45 |
| ONSEC | 000222 | 1/51 | 6/02 | 6/37 | 11/09 | 17/27 | 18/13 | |
| OPTR | 000203 | 1/37 | 12/23 | 13/02 | 15/46 | | | |
| OTAB | 010600 | 1/10 | 1/11 | 10/41 | 26/15 | | | |
| PEAK | 000215 | 1/46 | 16/53 | 18/07 | 20/28 | | | |
| PFINF | 000172 | 1/24 | 4/02 | 16/19 | | | | |
| PKVAL | 002101 | 18/08 | 18/09 | 18/46 | 20/16 | 20/17 | 20/24 | 20/25 |
| PNTS | 000204 | 1/38 | 6/35 | 6/36 | 6/40 | 6/41 | 6/45 | 6/46 |
| | | 18/25 | 18/26 | | | | | |
| PR | 001305 | 9/15 | 10/05 | | | | | |
| PRO | 001441 | 12/15 | 13/17 | 13/20 | 13/35 | 13/40 | | |
| PROA | 001540 | 13/23 | 13/30 | | | | | |
| PROB | 001374 | 11/24 | 11/30 | | | | | |
| PROC | 001403 | 11/21 | 11/32 | | | | | |
| PROD | 001552 | 13/32 | 13/42 | | | | | |
| PRODO | 001543 | 13/13 | 13/34 | | | | | |
| PR1 | 001435 | 12/10 | 13/54 | | | | | |
| PR2 | 001334 | 10/33 | 11/44 | | | | | |
| PR2C | 001351 | 11/02 | 11/06 | | | | | |
| PRCNT | 001424 | 11/51 | 12/07 | 13/19 | 13/31 | 13/34 | 13/37 | |

MAIN

| | | | | | | | |
|---|---|---|---|---|---|---|---|
| PRFLD | 000226 | 1/55 | 10/07 | 11/42 | 16/42 | | |
| PRLNG | 001422 | 11/49 | 12/05 | 13/53 | | | |
| PRMOF | 001570 | 12/23 | 13/11 | 13/58 | | | |
| PRPEN | 001421 | 10/15 | 11/43 | 11/48 | | | |
| PROG | 000207 | 1/06 | 3/36 | 3/37 | 3/38 | | |
| PRP | 001567 | 12/04 | 13/55 | 13/57 | | | |
| PRR | 001420 | 10/05 | 11/45 | 11/47 | | | |
| PRSG | 001645 | 12/34 | 15/05 | | | | |
| PRSGC | 001661 | 15/06 | 15/10 | 15/17 | | | |
| PRSGR | 001660 | 15/05 | 15/08 | 15/15 | 15/16 | | |
| PRX | 001425 | 11/16 | 11/53 | | | | |
| PR. | 001427 | 11/11 | 11/54 | 12/02 | | | |
| PTK | 001423 | 11/50 | 12/06 | 13/30 | 13/36 | | |
| PTZ | 000235 | 2/02 | 4/47 | 6/28 | 6/38 | 17/28 | 18/14 |
| PUT | 001222 | 8/49 | 8/52 | | | | |
| READ | 000276 | 1/17 | 1/19 | 15/12 | 10/21 | 21/16 | |
| RES | 000234 | 2/01 | 6/09 | 6/33 | 11/14 | 17/33 | 18/19 |
| SC0 | 001233 | 9/07 | 9/12 | | | | |
| SC1 | 001242 | 9/15 | | | | | |
| SCAL | 000216 | 1/47 | 4/40 | 9/06 | 9/13 | 12/27 | 16/51 |
| SCALE | 001226 | 7/28 | 7/31 | 9/01 | | | |
| SECL | 000237 | 2/04 | 6/03 | 6/11 | 6/13 | 6/15 | 6/18 | 6/20 |
| | | 7/13 | 11/19 | 16/45 | | | |
| SHFTK | 001571 | 12/29 | 13/59 | 15/37 | | | |
| SOFTL | 000227 | 1/56 | 10/34 | 17/25 | 18/11 | | |
| SPTR | 000214 | 1/45 | 4/59 | 5/10 | 5/11 | 9/04 | 9/07 | 9/10 |
| ST0 | 000605 | 3/09 | 3/17 | | | | |
| ST2A | 000621 | 3/22 | 3/27 | | | | |
| ST1B | 000616 | 3/11 | 3/19 | | | | |
| ST1 | 000654 | 3/28 | 4/02 | | | | |
| ST1A | 000701 | 4/19 | 4/24 | | | | |
| ST2 | 000742 | 5/02 | 5/14 | | | | |
| ST3 | 000763 | 5/21 | 5/25 | | | | |
| ST4 | 001004 | 5/39 | 5/42 | | | | |
| ST403 | 001212 | 4/25 | 5/46 | | | | |
| ST401 | 001215 | 4/48 | 5/50 | | | | |
| ST402 | 001224 | 4/17 | 6/08 | | | | |
| ST7 | 001067 | 7/02 | | | | | |
| ST18 | 012600 | 1/41 | 1/42 | 26/04 | | | |
| START | 000600 | 3/04 | | | | | |
| STE | 001143 | 3/47 | 8/02 | | | | |
| STE11 | 001163 | 3/51 | 8/18 | | | | |
| STE12 | 001165 | 5/32 | 6/24 | 8/20 | | | |
| STE2 | 001145 | 3/48 | 6/30 | 8/04 | | | |
| STE3 | 001147 | 5/23 | 8/06 | | | | |
| STE5 | 001151 | 7/23 | 7/27 | 7/30 | 8/08 | | |
| STE6 | 001153 | 3/49 | 8/10 | | | | |
| STE7 | 001155 | 3/50 | 8/12 | | | | |
| STE8 | 001157 | 7/06 | 8/14 | | | | |
| STE9 | 001161 | 7/15 | 8/16 | | | | |
| TCNT | 000223 | 1/52 | 4/24 | 5/16 | 6/21 | 10/14 | |
| TEXT | 001176 | 8/25 | 8/27 | 8/31 | | | |
| TEXTC | 001204 | 8/37 | 8/46 | 8/47 | | | |
| TEXTL | 001201 | 8/33 | 8/37 | 8/45 | 8/50 | | |
| TEXTP | 001220 | 8/44 | 8/49 | | | | |
| TEXTR | 001217 | 8/35 | 8/43 | 8/48 | | | |
| TF2 | 001610 | 14/18 | 14/34 | | | | |
| TF1 | 001624 | 14/28 | 14/32 | | | | |

```
 ??3: .MAIN
TFILL  ??1572     14/?4    26/21
TF?NT  ??1633    14/?9    14/33    14/4?
TFL?C  ??1632    14/?6    14/21    14/22    14/39
TFP    ??1631    14/?4    14/35    14/38
TFTMP  ??1634    14/17    14/23    14/32    14/41
TFSEC  ???232     1/59     6/25     7/14
TSCAT  ???236     2/?3     6/16    11/18
TSECT  ??0231     1/58     5/33     7/?5
T?PLO  ???2?2     1/34     1/35     1/36     1/37    1/38    1/39    1/40
                  1/41     1/42     1/43     1/44    1/45    1/46    1/47
                  1/48     1/49     1/50     1/51    1/52    1/53    1/54
                  1/55     1/56     1/57     1/58    1/59    1/60    2/?1
                  2/?2     2/?3     2/?4     2/?6    4/?3    4/?4    4/?5
APRS   ??1662    12/35    15/23
AP?SP  ??1676    15/29    15/35
AP?S1  ??1711    15/39    15/46
AP?S2  ??1703    15/4?    15/45
AP?S3  ??1721    15/51    15/54
AP?S4  ??170?    15/34    15/37
AP?SR  ??1724    15/23    15/53    15/56    15/57
AP?TF  ??0277     1/18     1/2?    13/47    22/28
XECFI  ??1635    14/46    26/20
XTFIL  ??0263     2/25    10/36    10/40
.FGET  ??1725    16/08    26/?7
```

What is claimed is:

1. A system for resolving a data sequence derived from a time-varying signal-generating phenomenon, said system comprising, in combination:
   means for repetitively initiating said phenomenon;
   means for detecting signals derived from said phenomenon during the course thereof;
   means for sampling said signals during a fixed time increment commencing a predetermined time interval following each initiation of said phenomenon;
   means for convolving said sampling of said signals with a transformation;
   means for selectively altering the temporal relation between initiation of said phenomenon and convolution of said signals so as to produce a time-ordered set of said samplings in which the sequence of the phenomenon and the convolution is temporally shifted in successive increments with respect to one another; and
   means for combining said samplings according to the order of said set so as to synthesize an interferogram representing the convolution with said transformation of the signals from said phenomenon at said fixed time position.

2. A system as defined in claim 1 wherein said means for convolving comprises a fast Fourier scanning interferometer.

3. A system as defined in claim 1 wherein said means for altering the temporal relation between initiation and convolution comprises:
   clock means for producing an electrical pulse train;
   means for controlling said means for convolving in accordance with the timing of said pulse train; and
   means for controlling said means for repetitively initiating in accordance with the timing of said pulse train.

4. A system as defined in claim 3 wherein said means for delaying comprises a first settable electrical counter.

5. A system as defined in claim 3 wherein said means for convolving and said clock means respectively comprise continuous scanning interferometers coupled to one another to scan together.

6. A system as defined in claim 5 including means for establishing said fixed time increment in accordance with the timing of said pulse train.

7. A system as defined in claim 6 wherein said means for establishing comprises a second settable electrical counter.

8. A system as defined in claim 3 wherein said means for sampling comprises a sample-and-hold circuit and analog-to-digital conversion means for converting the samples of said signal to digital form.

* * * * *